(12) United States Patent
Burke et al.

(10) Patent No.: US 7,138,122 B2
(45) Date of Patent: Nov. 21, 2006

(54) THERAPEUTIC SYSTEMS

(75) Inventors: Philip John Burke, Wiltshire (GB); Richard John Knox, Salisbury (GB)

(73) Assignee: Enzacta R & D Limited, London (GB)

( * ) Notice: Subject to any disclaimer, the term of this patent is extended or adjusted under 35 U.S.C. 154(b) by 537 days.

(21) Appl. No.: 10/099,830

(22) Filed: Mar. 13, 2002

(65) Prior Publication Data

US 2003/0086933 A1 May 8, 2003

Related U.S. Application Data

(63) Continuation of application No. 09/445,865, filed as application No. PCT/GB98/01731 on Jun. 15, 1998, now Pat. No. 6,867,231.

(30) Foreign Application Priority Data

Jun. 14, 1997 (GB) ................................ 9712370.7

(51) Int. Cl.
*A01N 43/00* (2006.01)
*A61K 31/33* (2006.01)

(52) U.S. Cl. .................... 424/181.1; 514/183; 514/485; 424/78.14

(58) Field of Classification Search ................ 548/272; 546/316; 514/183, 485; 424/78.14, 181.1
See application file for complete search history.

(56) References Cited

U.S. PATENT DOCUMENTS

| | | | |
|---|---|---|---|
| 4,440,859 A | 4/1984 | Rutter et al. | |
| 4,530,901 A | 7/1985 | Weissmann | |
| 4,582,800 A | 4/1986 | Crowl | |
| 4,677,063 A | 6/1987 | Mark et al. | |
| 4,678,751 A | 7/1987 | Goeddel | |
| 4,704,362 A | 11/1987 | Itakura et al. | |
| 4,710,463 A | 12/1987 | Murray | |
| 4,757,006 A | 7/1988 | Toole, Jr. et al. | |
| 4,766,075 A | 8/1988 | Goeddel et al. | |
| 4,810,648 A | 3/1989 | Stalker | |

FOREIGN PATENT DOCUMENTS

| | | |
|---|---|---|
| EP | 0 251 744 A2 | 1/1988 |
| EP | 0 258 067 A2 | 3/1988 |
| EP | 0 302 473 A2 | 2/1989 |
| EP | 0 415 731 A2 | 3/1991 |
| JP | 54060386 | 5/1979 |
| JP | 60184252 | 9/1985 |
| WO | WO 88/07378 A1 | 10/1988 |
| WO | WO 89/10140 A1 | 11/1989 |
| WO | WO 90/01063 A1 | 2/1990 |
| WO | WO 91/09867 A1 | 7/1991 |
| WO | WO 91/11201 A1 | 8/1991 |
| WO | WO 93/08288 A1 | 4/1993 |
| WO | WO 93/13805 A1 | 7/1993 |
| WO | WO 93/13806 A1 | 7/1993 |
| WO | WO 95/12678 A1 | 5/1995 |
| WO | WO 97/07097 A1 | 2/1997 |
| WO | WO 97/20580 A1 | 6/1997 |
| WO | WO 97/24143 A1 | 7/1997 |
| WO | WO 98/22577 A1 | 5/1998 |
| WO | WO 98/24478 A2 | 6/1998 |

OTHER PUBLICATIONS

Friedlos et al. (Biochemical Pharmacology 1992; 44: 25-31, IDS).*
Norris et al. (Can. J. Chem. 1977; 55: 1687-1695).*
Friedlos et al. #1 (Biochem. Pharmacol. 1992; 44: 1739-1743).*
Friedlos et al. #2 (Biochemical Pharmacology 1992; 44: 25-31).*
Jaiswal (J. Biol. Chem. 1994; 269; 14502-14508).*
Anlezark, et al., "The bioactivation of 5-(aziridin-1-yl)-2,4-dinitrobenzamide (CB1954)—I. Purification and properties of a nitroreductase enzyme from *Escherichia coli*—a potential enzyme for antibody-directed enzyme prodrug therapy (ADEPT)," *Biochem. Pharmacol.* 1992 44(12):2289-95.
Better, et al., "*Escherichia coli* secretion of an active chimeric antibody fragment," *Science* 240(4855):1041-43 (1988).
Bird, et al., "Single-chain antigen-binding proteins," *Science* 242(4877):423-26 (1988).
Bischoff, et al., "An adenovirus mutant that replicates selectively in p53-deficient human tumor cells," *Science* 274(5286):373-76 (1996).
Boland, et al., "The differences in kinetics of rat and human DT diaphorase result in a differential sensitivity of derived cell lines to CB 1954 (5-(aziridin-1-yl)-2,4-dinitrobenzamide)," *Biochem. Pharmacol.* 41(6-7):867-75 (1991).
Bradl, et al., "Malignant melanoma in transgenic mice," *Proc. Natl. Acad. Sci. U. S. A.* 88(1):164-68 (1991).
Brawer, "Prostate specific antigen. A review," *Acta. Oncol.* 30(2):161-68 (1991).
Chen, et al., "Expression of rat liver NAD(P)H:quinone-acceptor oxidoreductase in *Escherichia coli* and mutagenesis in vitro at Arg-177," *Biochem. J.* 284 (Pt 3):855-60 (1992).

(Continued)

*Primary Examiner*—Jeffrey Siew
*Assistant Examiner*—Brandon Fetterolf
(74) *Attorney, Agent, or Firm*—Pabst Patent Group LLP

(57) ABSTRACT

A compound comprising a target cell-specific portion and human NAD(P)H:quinone reductase 2 (NQO2) or a variant or fragment or fusion or derivative thereof which has substantially the same activity as NQO2 towards a given prodrug, or a polynucleotide encoding said NQO2 or said variant or fragment or fusion or derivative. A recombinant polynucleotide comprising a target cell-specific promoter operably linked to a polynucleotide encoding human NAD(P)H:quinone reductase 2 (NQO2) or a variant or fragment or fusion or derivative thereof which has substantially the same activity as NQO2 towards a given prodrug. The compounds and polynucleotides are useful in a method of treating a patient in conjunction with a suitable prodrug. A method of treating a human patient with a target cell to be destroyed wherein the target cell expresses NQO2 the method comprising administering to the patient a prodrug which is converted to a substantially cytotoxic drug by the action of NQO2 and nicotinamide riboside (reduced) (NRH) or an analogue thereof which can pass reducing equivalents to NQO2.

6 Claims, 19 Drawing Sheets

OTHER PUBLICATIONS

Chen, et al., "Molecular basis of the catalytic differences among DT-diaphorase of human, rat, and mouse," *J. Biol. Chem.* 272(3):1437-39 (1997).

Clark, et al., "Role of the Bp35 cell surface polypeptide in human B-cell activation," *Proc. Natl. Acad. Sci. U. S. A.* 82(6):1766-70 (1985).

Connors & Wisson, "Cure of mice bearing advanced plasma cell tumours with aniline mustard: the relationship between glucuronidase activity and tumour sensitivity," *Nature* 210(38):866-67 (1966).

Corvalan & Smith, "Construction and characterisation of a hybrid-hybrid monoclonal antibody recognising both carcinoembryonic antigen (CEA) and vinca alkaloids," *Cancer Immunol. Immunother.* 24(2):127-32 (1987).

Corvalan, et al., "Increased therapeutic effect of vinca alkaloids targeted to tumour by a hybrid-hybrid monoclonal antibody," *Cancer Immunol. Immunother.* 24(2):138-43 (1987).

Corvalan, et al., "Specific in vitro and in vivo drug localisation to tumour cells using a hybrid-hybrid monoclonal antibody recognising both carcinoembryonic antigen (CEA) and vinca alkaloids," *Cancer Immunol. Immunother.* 24(2):133-37 (1987).

Cotten, et al., "High-efficiency receptor-mediated delivery of small and large (48 kilobase gene constructs using the endosome-disruption activity of defective or chemically inactivated adenovirus particles," *Proc. Natl. Acad. Sci. U. S. A.* 89(13):6094-98 (1992).

Coussens, et al., "Tyrosine kinase receptor with extensive homology to EGF receptor shares chromosomal location with neu oncogene," *Science* 230(4730):1132-39 (1985).

Culver, et al., "In vivo gene transfer with retroviral vector-producer cells for treatment of experimental brain tumors," *Science* 256(5063):1550-52 (1992).

Curiel, "Adenovirus facilitation of molecular conjugate-mediated gene transfer," *Prog. Med. Virol.* 40:1-18 (1993).

Dermer, "Another Anniversary for the War on Cancer," *Bio/Technology* 12:230 (1994).

Drabek, et al., "The expression of bacterial nitroreductase in transgenic mice results in specific cell killing by the prodrug CB1954," *Gene Ther.* 4(2):93-100 (1997).

Freshney, *Culture of Animal Cells: A Manual of Basic Technique*, Alan R. Liss, Inc., p. 4, (New York, 1983).

Friedlos & Knox, "Metabolism of NAD(P)H by blood components. Relevance to bioreductively activated prodrugs in a targeted enzyme therapy system," *Biochem. Pharmacol.* 44(4):631-35 (1992).

Friedlos, et al., "Identification of novel reduced pyridinium derivatives as synthetic co-factors for the enzyme DT diaphorase (NAD(P)H dehydrogenase (quinone), EC 1.6.99.2)," *Biochem. Pharmacol.* 44(1):25-31 (1992).

Friedlos, et al., "Potentiation of CB 1954 cytotoxicity by reduced pyridine nucleotides in human tumour cells by stimulation of DT diaphorase activity," *Biochem. Pharmacol.* 44(9):1739-43 (1992).

Gilliland, et al., "Universal bispecific antibody for targeting tumor cells for destruction by cytotoxic T cells," *Proc. Natl. Acad. Sci. U. S. A.* 85(20):7719-23 (1988).

Green, et al., "Sensitization of colorectal and pancreatic cancer cell lines to the prodrug 5-(aziridin-1-yl)-2,4-dinitrobenzamide (CB1954) by retroviral transduction and expression of the *E. coli* nitroreductase gene," *Cancer Gene Ther.* 4(4):229-38 (1997).

Gura, "Systems for Identifying New Drugs are Often Faulty," *Science* 278:1041-42 (1997).

Harwood, et al., "Comparative tumour localization of antibody fragments and intact IgG in nude mice bearing a CEA-producing human colon tumour xenograft," *Eur. J. Cancer Clin. Oncol.* 21(12):1515-22 (1985).

Hellström, et al., "Monoclonal mouse antibodies raised against human lung carcinoma," *Cancer Res.* 46(8):3917-23 (1986).

Hurrell, "Monoclonal Hybridoma Antibodies: Techniques and Applications," (CRC Press).

Huston, et al., "Protein engineering of antibody binding sites: recovery of specific activity in an anti-digoxin single-chain Fv analogue produced in *Escherichia coli*," *Proc. Natl. Acad. Sci. U. S. A.* 85(16):5879-83 (1988).

Jackson, et al., "The tyrosinase-related protein-1 gene has a structure and promoter sequence very different from tyrosinase," *Nucleic Acids Res.* 19(14):3799-804 (1991.

Jaiswal, "Human NAD(P)H:quinone oxidoreductase2. Gene structure, activity, and tissue-specific expression," *J. Biol. Chem.* 269(20):14502-08 (1994).

Jaiswal, "Nucleotide and deduced amino acid sequence of a human cDNA (NQO2) corresponding to a second member of the NAD(P)H:quinone oxidoreductase gene family. Extensive polymorphism at the NQO2 gene locus on chromosome 6," *Biochemistry.* 29(7):1899-906 (1990).

Khan & Ross, "Tumour-growth inhibitory nitrophenylaziridines and related compounds: structure-activity relationships," *Chem. Biol. Interact.* 1(1):27-47 (1969).

Knox, et al., "The bioactivation of 5-(aziridin-1-yl)-2,4-dinitrobenzamide (CB1954)—II. A comparison of an *Escherichia coli* nitroreductase and Walker DT diaphorase," *Biochem. Pharmacol.* 44(12):2297-301 (1992).

Knox, et al., "The bioactivation of CB 1954 and its use as a prodrug in antibody-directed enzyme prodrug therapy (ADEPT)," *Cancer Metastasis Rev.* 12(2):195-212 (1993).

Knox, et al., "Virtual cofactors for an *Escherichia coli* nitroreductase enzyme: relevance to reductively activated prodrugs in antibody directed enzyme prodrug therapy (ADEPT)," *Biochem. Pharmacol.* 49(11):1641-47 (1995).

Kuriyama, et al., "A potential approach for gene therapy targeting hepatoma using a liver-specific promoter on a retroviral vector," *Cell Struct. Funct.* 16(6):503-10 (1991).

Laemmli, "Cleavage of structural proteins during the assembly of the head of bacteriophage T4," *Nature* 227(259):680-5 (1970).

Ledley, "Nonviral gene therapy: the promise of genes as pharmaceutical products," *Hum. Gene Ther.* 6(9):1129-44 (1995).

Liao & Williams-Ashman, "Enzymatic oxidation of some non-phosphorylated derivatives of dihydronicotinamide," *Biochem. and Biophys. Res. Comm.* 4:208-13 (1961).

Liao & Williams-Ashman, "Inhibition of the enzymic oxidation of some dihydropyridines by polycyclic aromatic hydrocarbons," *Biochem. Pharmacol.* 6:53-54 (1961).

Liao, et al., "Purification and properties of a flavoprotein catalyzing the oxidation of reduced ribosyl nicotinamide," *J. Biol. Chem.* 237:2981-87 (1962).

Lundwall, "Characterization of the gene for prostate-specific antigen, a human glandular kallikrein," *Biochem. Biophys. Res. Commun.* 161(3):1151-9 (1989).

Martin & Papahajopoulos, et al., "Irreversible coupling of Immunoglobulin fragments to preformed vesicles. An improved method for liposome targeting," *J. Biol. Chem.* 257(1):286-8 (1982).

Mauger, et al., "Self-immolative prodrugs: candidates for antibody-directed enzyme prodrug therapy in conjunction with a nitroreductase enzyme," *J. Med. Chem.* 37(21):3452-58 (1994).

Michael, et al., "Addition of a short peptide ligand to the adenovirus fiber protein," *Gene Ther.* 2(9):660-68 (1995).

Miller & Vile, "Targeted vectors for gene therapy," *FASEB J.* 9(2):190-99 (1995).

Morrison, et al., "Chimeric human antibody molecules: mouse antigen-binding domains with human constant region domains," *Proc. Natl. Acad. Sci. U. S. A.* 81(21):6851-55 (1984).

Nassander, et al., "In vivo targeting of OV-TL 3 immunoliposomes to ascitic ovarian carcinoma cells (OVCAR-3) in athymic nude mice," *Cancer Res.* 52(3):646-53 (1992).

Neuberger, et al., "Recombinant antibodies possessing novel effector functions," *Nature* 312(5995):604-08 (1984).

O'Sullivan, et al., "Comparison of two methods of preparing enzyme-antibody conjugates: application of these conjugates for enzyme immunoassay," *Anal. Biochem.* 100(1):100-08 (1979).

Quinn, "Studies on CB1954 and its analogues," A thesis submitted for the degree of Doctor of Philosophy to the University of London, 1996.

Riegman, et al., "Characterization of the prostate-specific antigen gene: a novel human kallikrein-like gene," *Biochem. Biophys. Res. Commun.* 159(1):95-102 (1989).

Saiki, et al., "Primer-directed enzymatic amplification of DNA with a thermostable DNA polymerase," *Science* 239(4839):487-91 (1988).

Sambrook, et al., *Molecular Cloning: A Laboratory Manual* Cold Spring Harbor Laboratory Press, Cold Spring Harbor:New York (1989).

Schrewe, et al., "Cloning of the complete gene for carcinoembryonic antigen: analysis of its promoter indicates a region conveying cell type-specific expression," *Mol. Cell. Biol.* 10(6):2738-48 (1990).

Sharma, et al., "Inactivation and clearance of an anti-CEA carboypeptidase G2 conjugate in blood after localisation in a xenograft model," *Br. J. Cancer.* 61(5):659-62 (1990).

Sherwood, "Advanced drug delivery reviews: enzyme prodrug therapy," *Adv. Drug Del. Rev.* 22:269-88 (1996).

Skerra, et al., "Assembly of a functional immunoglobulin Fv fragment in *Escherichia coli*," *Science* 240(4855):1038-41 (1988).

Trowell, "The cytocidal action of mitotic poisons on lymphocytes *in vitro*," *Biochemical Pharmacology* 5:53-63 (1960).

Wagner, et al., "Transferrin-polycation conjugates as carriers for DNA uptake into cells," *Proc. Natl. Acad. Sci. U. S. A.* 87(9):3410-14 (1990).

Ward, et al., "Binding activities of a repertoire of single immunoglobulin variable domains secreted from *Escherichia coli*," *Nature* 341(6242):544-46 (1989).

Whisson & Connors, "Cure of mice bearing advanced plasma cell tumours with aniline mustard," *Nature* 206(985):689-91 (1965).

Winter & Milstein, "Man-made antibodies," *Nature* 349(6307):293-99 (1991).

Wu, et al., "Catalytic properties of NAD(P)H:quinone oxidoreductase-2 (NQO2), a dihydronicotinamide riboside dependent oxidoreductase," *Arch. Biochem. Biophys.* 347(2):221-28 (1997).

Zola, "Monoclonal Antibodies: A manual of techniques," (CRC Press, 1988).

Isitani, et al., "Redox-photosensitized reactions. 13. Ru(bpy)3 2+-Photosensitized reaction of an NADH model, 1-benzyl-1,4-dihydronicotinamide, with aromatic carbonyl compounds and comparison with thermal reactions" *J. Org. Chem.* 52: 2790-2796 (1987).

Meijer, et al., "Cyclopropane ring as a chemical probe in the study of the mechanism of hydrogen transfer by 1,4-dihydropyridine derivatives" *Tetrahedron Letters* 40(24): 5185-5195 (1984).

Melton, et al., "Antibody-directed enzyme prodrug therapy (ADEPT)" *Drugs of the Future* 21(2): 167-181 (1996).

Pierre, et al., "An artificial allosteric system: regulation of a biomimetic reduction (NADH model) by potassium ions" *Tetrahedron Letters* 33(2): 217-220 (1992).

\* cited by examiner $C_{11}H_{16}N_2O_5$
256.25
256.105921
C 51.6% H 6.3% N 10.9% O 31.2%

```
                                                                                                                     v
ATGGCAGGTAAGAAAGTACTCATTGTCTATGCAACCAGGAACCCAAGTCTTTCAACGGATCCTTGAAGA                                                245
 M  A  G  K  K  V  L  I  V  Y  A  H  Q  E  P  K  S  F  N  G  S  L  K  N
                                                                                                                     v
ATGTGGCTGTAGATGAACTGAGCAGGCAGGCTGCACGTCACAGTGTCTGATTTGTATGCCATGAACTT                                                 315
 V  A  V  D  E  L  S  R  Q  G  C  T  V  T  V  S  D  L  Y  A  M  N  F                                                  4
                                                                                                                     v
TGAGCCGAGGGCCACAGACAAAGATATCACTGGTACTCTTCTAATCCTGAGGTTTCAATTATGGAGTG                                                 385
 E  P  R  A  T  D  K  D  I  T  G  T  L  S  N  P  E  V  F  N  Y  G  V                                                 70
                                                                                                                     v
GAAACCCACGAAGCCTACAAGCAAAGGTCTCTGGCTAGCGACATCACTGATGAGCAGAAAAAGGTTCGGG                                               455
 E  T  H  E  A  Y  K  Q  R  S  L  A  S  D  I  T  D  E  Q  K  K  V  R  E
                                                                                                                     v
AGGCTGACTAGTGATATTTCAGTTCCGCTGTACTGGTTCAGCGTGCCGCCATCCTGAAGGGCTGGAT                                                  525
 A  D  L  V  I  F  Q  F  F  P  L  Y  W  F  S  V  P  A  I  L  K  G  W  M                                              11
                                                                                                                     v
GGATAGGGTGCTGTGCCAGGGCTTTGCCTTTGACATCCCAGGATTCTACGATTCCGGTTTGCTCCAGGGT                                               595
 D  R  V  L  C  Q  G  F  A  F  D  I  P  G  F  Y  D  S  G  L  L  Q  G                                                140
                                                                                                                     v
AAACTAGCGCTCCTTTCCGTAACCACGGAGGCCGAGATGTACACGAAGACAGGAGTCAATGGAG                                                     665
 K  L  A  L  L  S  V  T  T  G  G  T  A  E  M  Y  T  K  T  G  V  N  G  D                                               1
                                                                                                                     v
ATTCTCGATACTTCCTGTGGCCACTCCAGCATGGCACATTACACTTCTGTGGATTAAAGTCCTTGCCCC                                                735
 S  R  Y  F  L  W  P  L  Q  H  G  T  L  H  F  C  G  F  K  V  L  A  P                                                 18
                                                                                                                     v
TCAGATCAGCTTTGCTCCTGAAATTGCATCCGAAGAAGAAAGGGGATGGTGGCTGCTGGTCCCAG                                                    805
 Q  I  S  F  A  P  E  I  A  S  E  E  E  R  R  K  G  M  V  A  A  W  S  Q                                             210
                                                                                                                     v
AGGCTGCAGACCATCTGGAAGGAAGAGCCCATCCCCTGCACAGCCCACTGGCACTTCGGGCAATAACT                                                 873
 R  L  Q  T  I  W  K  E  E  P  I  P  C  T  A  H  W  H  F  G  Q  <                                                   231
```

*Fig. 6*

| Compound number | R |
|---|---|
| 1 | -CH₂CH₂CH₂SO₃⁻ |
| 2 | -CH₂CONH₂ |
| 3 | -CH₂CH₂CH₃ |
| 4 | -CH(CH₃)₂ |
| 5 | -CH₂CH₂CH₂OH |
| 6 | -CH₂CH₂OH |
| 7 | -CH₂CH₂COOH |
| 8 | -CH₂C₆H₅ |
| 9 | -CH₃ |
| 10 | -CH₂CH₃ |
| 11 | -CH₂CH₂C₆H₅ |

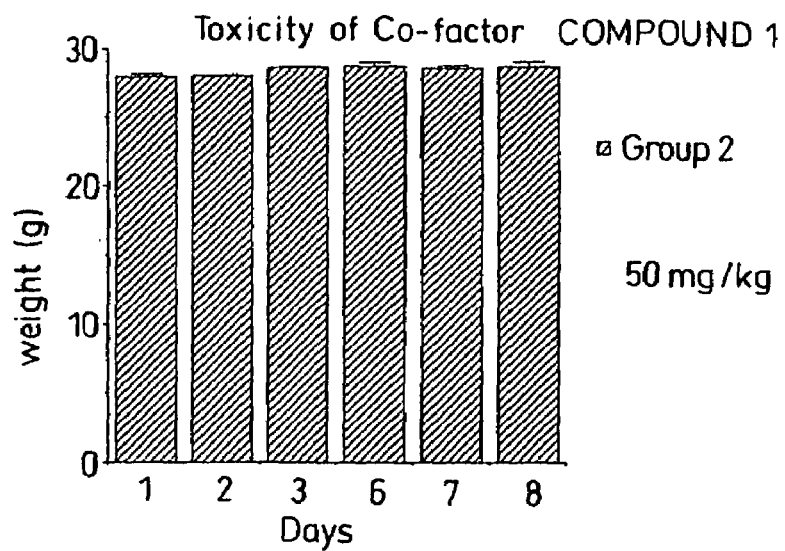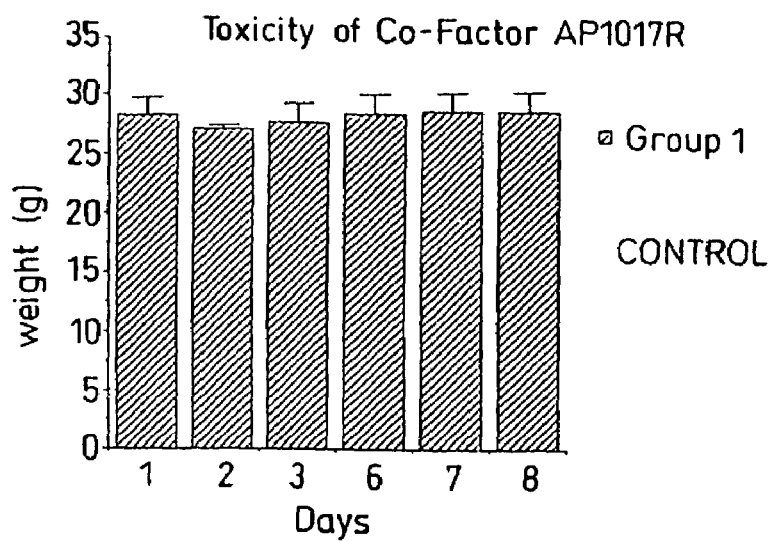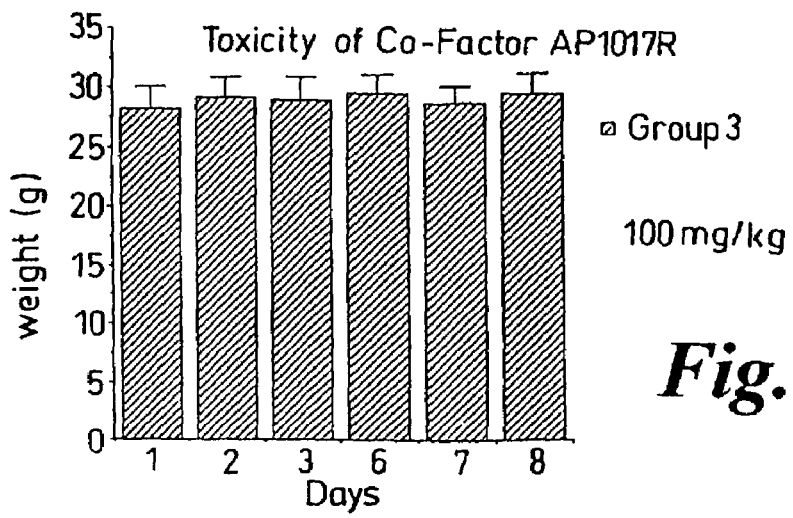
Fig. 16

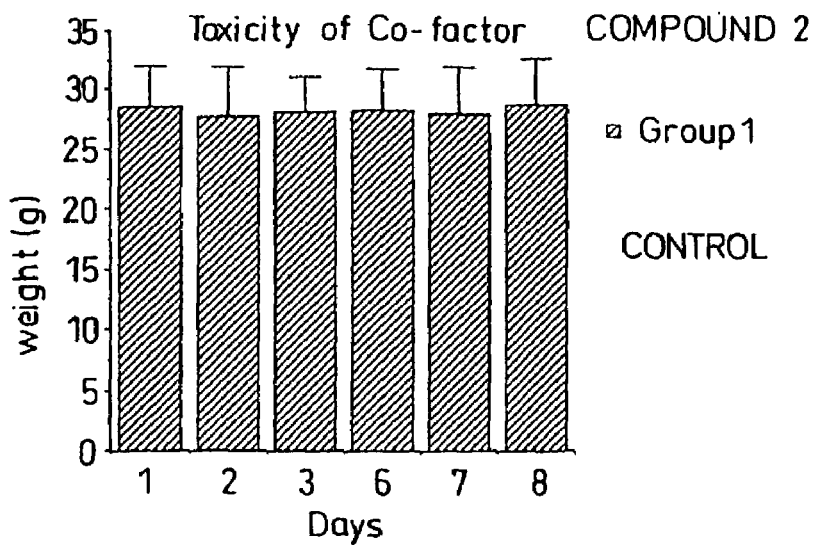
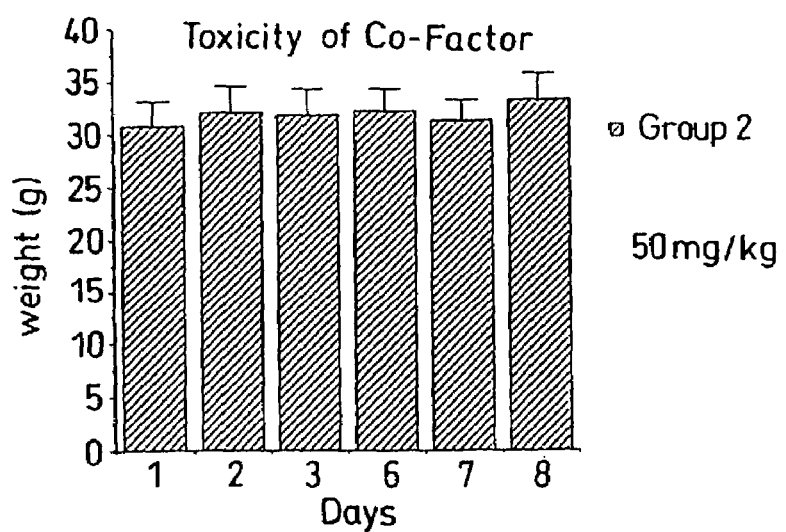
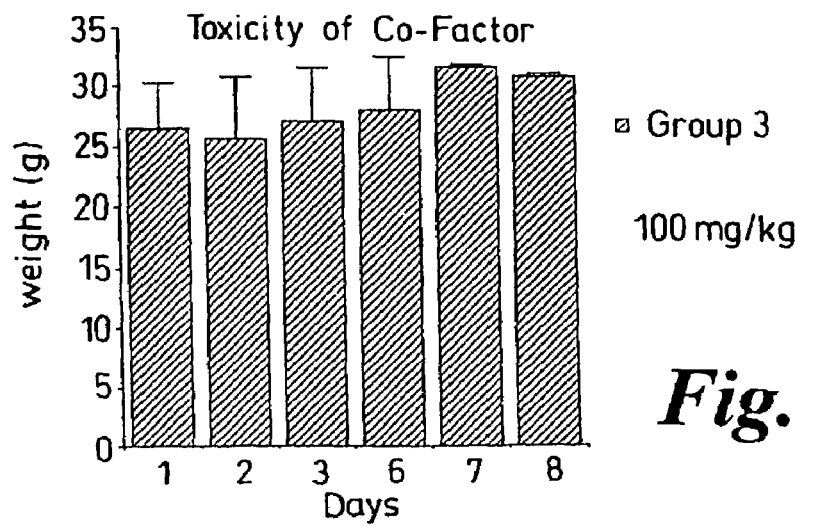
Fig. 17

THERAPEUTIC SYSTEMS

CROSS-REFERENCE TO RELATED APPLICATIONS

This application is a continuation of prior application Ser. No. 09/445,865 filed Feb. 11, 2000 now U.S. Pat. No. 6,867,231, entitled "Therapeutic Systems", by Philip John Burke and Richard John Knox, which is a 371 of International Application No. PCT/GB98/01731 filed in the United Kingdom Receiving Office for the Patent Cooperation Treaty on Jun. 15, 1998, which claims priority to British application No. GB9712370.7 filed on Jun. 14, 1997.

The present invention relates to therapeutic systems, particularly therapeutic systems for activating prodrugs and for the use of such systems in killing target cells, particularly tumour cells.

The delivery of a cytotoxic agent to the site of tumour cells is much desired because systemic administration of these agents can result in the killing of normal cells within the body as well as the tumour cells. The resulting toxicity to normal cells limits the dose of the cytotoxic agent and thus reduces the therapeutic potential of these agents. However, in some instances the administered agent has no intrinsic activity but is converted in vivo at the appropriate time or place to the active drug. Such analogues are referred to as prodrugs and are used extensively in medicine [Connors and Knox, 1995]. Conversion of the prodrug to the active form can take place by a number of mechanisms depending, for example, on changes of pH, oxygen tension, temperature or salt concentration or by spontaneous decomposition of the drug or internal ring opening or cyclisation.

WO 88/07378 describes a two-component system, and therapeutic uses thereof, wherein a first component comprises an antibody fragment capable of binding with a tumour-associated antigen and an enzyme capable of converting a pro-drug into a cytotoxic drug, and a second component which is a pro-drug which is capable of conversion to a cytotoxic drug. This general system, which is often referred to as "antibody-directed enzyme pro-drug therapy" (ADEPT), is also described in relation to specific enzymes and pro-drugs in EP 0 302 473 and WO 91/11201.

WO 89/10140 describes a modification to the system described in WO 88/07378 wherein a further component is employed in the system. This further component accelerates the clearance of the first component from the blood when the first and second components are administered clinically. The second component is usually an antibody that binds to the antibody-enzyme conjugate and accelerates clearance. An antibody which was directed at the active site on the enzyme had the additional advantage of inactivating the enzyme. However, such an inactivating antibody has the undesirable potential to inactivate enzyme at the tumour sites, but its penetration into tumours was obviated by the addition of galactose residues to the antibody. The galactosylated antibody was rapidly removed from the blood, together with bound antibody-enzyme component, via galactose receptors in the liver. The system has been used safely and effectively in clinical trials. However, galactosylation of such an inactivating antibody which results in its rapid clearance from blood also inhibits its penetration of normal tissue and inactivation of enzyme localised there.

WO 93/13805 describes a system comprising a compound comprising a target cell-specific portion, such as an antibody specific to tumour cell antigens, and an inactivating portion, such as an enzyme, capable of converting a substance which in its native state is able to inhibit the effect of a cytotoxic agent into a substance which has less effect against said cytotoxic agent. The prolonged action of a cytotoxic agent at tumour sites is therefore possible whilst protecting normal tissues from the effects of the cytotoxic agent.

WO 93/13806 describes a further modification of the ADEPT system comprising a three component kit of parts for use in a method of destroying target cells in a host. The first component comprises a target cell-specific portion and an enzymatically active portion capable of converting a pro-drug into a cytotoxic drug; the second component is a pro-drug convertible by said enzymatically active portion to the cytotoxic drug; and the third component comprises a portion capable of at least partly restraining the component from leaving the vascular compartment of a host when said component is administered to the vascular compartment, and an inactivating portion capable of converting the cytotoxic drug into a less toxic substance.

Our unpublished but co-pending patent application GB 9624993.3 describes a macromolecule prodrug therapy system. Our unpublished but co-pending patent application PCT/GB96/03000 describes the use of enzyme inhibitors in an improvement of ADEPT; and our unpublished but co-pending patent application PCT/GB96/03254 describes the use of internalising antibodies and/or intracellular cofactors in an improvement to ADEPT.

EP 0 415 731 describes a therapeutic system which is often called GDEPT (gene-directed enzyme prodrug therapy).

A major approach in prodrug design is the synthesis of inert analogues which are converted to the active drug by enzyme action. In cancer chemotherapy prodrugs have been used clinically for a variety of purposes ranging from analogues with better formulation properties to prodrugs designed to be selectively activated in the tumour environment. Results from animal experiments and dose intensification studies in humans have indicated that some tumour types, eg ovarian cancer, might be completely eradicated by chemotherapy if the dose of anti-cancer agent to which they respond could be increased by a hundred-fold. Attempts to increase the dose administered using dose intensification, by autologous bone marrow transplantation after high doses of myelotoxic therapy, by rescue experiments eg folinic acid after methotrexate or by isolated limb perfusions, do allow a greater total dose to be given but not by this order of magnitude. However, there are many examples where this level of dose intensity can theoretically be achieved by using prodrugs which are selectively activated by enzymes present in tumours. Experiments on tumour bearing animals have shown that when a prodrug is activated uniquely in the tumour environment, cures can be obtained for mice bearing large primary tumours and extensive metastases [Connors and Whisson, 1966, Whisson and Connors, 1965]. Given that the prodrug is a good substrate for the enzyme specifically expressed in the tumour and that the difference in toxicity between prodrug and drug is a hundred-fold or more then, once a candidate enzyme has been identified (especially if there is also a high concentration of the enzyme in the extracellular spaces of the tumour), many different classes of anti-cancer agent can often be derivatised to form appropriate prodrugs. This can be demonstrated in approaches used to design prodrugs of cytotoxic alkylating agents. Because this class of anti-cancer agent acts predominantly but probably not exclusively by covalent alkylation of adjacent strands of DNA the first basic requirement for cytotoxicity is that the agent should have an optimal level of chemical reactivity which enables it to reach the tumour site after injection and be reactive enough to alkylate DNA. If the reagent is too reactive it may hydrolyse before reaching the tumour and if too unreactive may be excreted before sufficient DNA alkylation has taken place. Secondly, it must be able to pass through the endothelium and the cell and nuclear membranes to reach its target. Finally, because the predominant reaction that leads to cytotoxicity is a cross-linking reaction, then the alkylating agent must have a minimum of two alkylating arms.

In order to design an appropriate prodrug, once a unique tumour enzyme has been identified, a prodrug is synthesised which is lacking one or more of the features described but is acted upon by the enzyme to produce an appropriate drug. Thus, many alkylating prodrugs are chemically unreactive and non-toxic but are substrates for enzymes which metabolise them to highly reactive and toxic products. The ability of an alkylating agent to react with biological molecules depends on a minimal level of chemical reactivity and this level of activity can vary greatly depending on chemical structure. Small changes in electron donating or withdrawing properties can greatly alter chemical reactivity. Large numbers of anti-tumour alkylating agents have been tested experimentally and, almost without exception, active derivatives must be at least difunctional, ie have at least two alkylating arms.

Monofunctional agents, although they may be carcinogens, usually are much less toxic and if they can be converted enzymatically to difunctional agents might be effective prodrugs. An example of this is CB 1954 a monofunctional aziridine which was highly effective against the rat Walker tumour which is normally only sensitive to difunctional alkylating agents (reviewed by Knox et al, 1993). This tumour has a relatively high concentration of the enzyme DT-diaphorase (NQO1, EC 1.6.99.2) which reduces the 4-nitro group to a hydroxylamine which is then converted (probably by acetyl CoA) to a difunctional agent (FIG. 1). However, the human form of DT-diaphorase reduces CB 1954 much more slowly than the rat form and human tumours (even those containing the same levels of DT-diaphorase as rat Walker tumour) are resistant to this agent [Knox et al, 1993]. The difference in reduction rate is mostly due to a single amino-acid change, a glutamine to a tyrosine at amino acid position 104 [Chen et al, 1997]. Given the provenance of CB 1954 against rat tumours, a number of ways of activating CB 1954 in human tumours have been suggested. The first is antibody directed enzyme prodrug therapy (ADEPT, as mentioned above) in which an antibody is used to localise an *E. coli* nitroreductase at a tumour. This nitroreductase can reduce CB 1954 much more rapidly than rat DT-diaphorase. The system is described in WO 93/08228. Gene directed enzyme prodrug therapy (GDEPT) is a method by which the gene encoding for the nitroreductase from *Escherichia coli* is expressed in tumour cells and thus confers sensitivity to CB 1954. This is described in WO 95/12678.

It has also been reported that CB 1954 cytotoxicity can be dramatically increased in human cells by stimulating their endogenous DT-diaphorase with NRH [Friedlos et al, 1992a]. In these experiments, the toxicity of CB 1954 (5-(aziridin-1-yl)-2,4-dinitrobenzamide) towards human cells was greatly enhanced by NADH (when foetal calf serum was present in the culture medium) and by nicotinamide riboside (reduced) (NRH), but not by nicotinate riboside (reduced). Co-treatment of human cells with CB 1954 and NADH resulted in the formation of crosslinks in their DNA. The toxicity produced by other DNA crosslinking agents was unaffected by reduced nicotinamide compounds. When caffeine was included in the medium a reduction of the cytotoxicity of CB 1954 occurred. The toxicity experienced by human cell lines after exposure to CB 1954 and NADH was proportional to their levels of the enzyme DT diaphorase. It was concluded that NRH, which has been shown to be a cofactor for rat DT diaphorase [Friedlos et al, 1992b], is generated from NADH by enzymes in foetal calf serum [Friedlos and Knox, 1992] and stimulates the activity of human DT diaphorase towards CB 1954. However, it has recently been shown that there is an additional CB1954-reducing activity detectable in human cells in the presence of NRH and that this activity is much greater than that attributable to DT-diaphorase [Quinn, 1996].

The terms "nicotinamide mononuclcoside-reduced", "dihydronicotinamide riboside", "nicotinamide riboside (reduced)" and "NRH" are all equivalent and are used interchangeably in the patent specification. Nicotinamide riboside may be produced enzymatically from its commercially available mononucleotides using methods well known in the art, including those described in Friedlos & Knox (1992) *Biochem. Pharmacol.* 44, 631–635 which is incorporated herein by reference.

Human NAD(P)H:quinone oxidoreductase2 (NQO2) was identified by its homology to DT-diaphorase (NQO1) [Jaiswal et al, 1990]. The last exon in the NQO2 gene is 1603 bp shorter than the last exon of the NQO1 gene and encodes for 58 amino acids as compared to 101 amino acids encoded by the NQO1 gene. This makes the NQO2 protein 43 amino acids shorter than. the NQO1 protein. The high degree of conservation between NQO2 and NQO1 gene organization and sequence confirmed that the NQO2 gene encoded for a second member of the NQO gene family in humans but it lacked the quinone-reductase activity characteristic of DT-diaphorase [Jaiswal, 1994]. The NQO2 cDNA-derived protein expressed in monkey kidney COS 1 cells efficiently catalyzed nitroreduction of CB 10-200, an analogue of CB 1954 [Jaiswal, 1994]. Northern blot analysis indicated that the NQO2 gene was expressed in human heart, brain, lung, liver, and skeletal muscle but did not express in placenta. In contrast, the NQO1 gene was expressed in all human tissues. Large variations were noticed for expression of the NQO2 and NQO1 genes among various tissues [Jaiswal, 1994].

We have now shown that NQO2 can rapidly reduce CB1954 and consider this enzyme, not DT diaphorase, to be responsible for the potentiating effects of NRH on CB1954 cytotoxicity toward human cells reported by Friedlos et al [1992a].

Although all of the aforementioned methods of killing a target cell, such as a tumour cell, in an animal body are useful, it is still desirable to provide new systems of treatment.

A first aspect of the invention provides a compound comprising a target cell-specific portion and (a) human NAD(P)H:quinone reductase 2 (NQO2) or a variant or fragment or fusion or derivative thereof which has substantially the same activity as NQO2 towards a given prodrug, or (b) a polynucleotide encoding said NQO2 or said variant or fragment or fusion or derivative.

The entity which is recognised by the target cell-specific portion may be any suitable entity which is expressed by tumour cells, virally-infected cells, pathogenic microorganisms, cells introduced as part of gene therapy or normal cells of the body which one wishes to destroy for a particular reason. The entity should preferably be present or accessible to the targeting portion in significantly greater concentrations in or on cells which are to be destroyed than in any normal tissues of the host that cannot be functionally replaced by other therapeutic means. Use of a target expressed by a cancer cell would not be precluded, for example, by its equal or greater expression on an endocrine tissue or organ. In a life-saving situation the organ could be sacrificed provided its function was either not essential to life, for example in the case of the testes, or could be supplied by hormone replacement therapy. Such considerations would apply, for instance, to the thyroid gland, parathyroids, adrenal cortex and ovaries.

The entity which is recognised will often be an antigen. Tumour-associated antigens, when they are expressed on the cell membrane or secreted into tumour extra-cellular fluid, lend themselves to the role of targets for antibodies.

The antigen-specific portion may be an entire antibody (usually, for convenience and specificity, a monoclonal antibody), a part or parts thereof (for example an Fab fragment or F(ab')$_2$) or a synthetic antibody or part thereof. A conjugate comprising only part of an antibody may be advantageous by virtue of optimizing the rate of clearance from the blood and may be less likely to undergo non-specific binding due to the Fc part. Suitable monoclonal antibodies to selected antigens may be prepared by known techniques, for example those disclosed in "Monoclonal Antibodies: A manual of techniques", H. Zola (CRC Press, 1988) and in "Monoclonal Hybridoma Antibodies; Techniques and Applications", J. G. R. Hurrell (CRC Press, 1982). All references mentioned in this specification are incorporated herein by reference. Bispecific antibodies may be prepared by cell fusion, by reassociation of monovalent fragments or by chemical cross-linking of whole antibodies, with one part of the resulting bispecific antibody being directed to the cell-specific antigen and the other to the enzyme. The bispecific antibody can be administered bound to the enzyme or it can be administered first, followed by the enzyme. It is preferred that the bispecific antibodies are administered first, and after localization to the tumour cells, the enzyme is administered to be captured by the tumour localized antibody. Methods for preparing bispecific antibodies are disclosed in Corvalan et al (1987) *Cancer Immunol. Immunother.* 24, 127–132 and 133–137 and 138–143, and Gillsland et al (1988) *Proc. Natl. Acad. Sci. USA* 85, 7719–7723.

The variable heavy ($V_H$) and variable light ($V_L$) domains of the antibody are involved in antigen recognition, a fact first recognised by early protease digestion experiments. Further confirmation was found by "humanisation" of rodent antibodies. Variable domains of rodent origin may be fused to constant domains of human origin such that the resultant antibody retains the antigenic specificity of the rodent parented antibody (Morrison et al (1984) *Proc. Natl. Acad. Sci. USA* 81, 6851–6855).

That antigenic specificity is conferred by variable domains and is independent of the constant domains is known from experiments involving the bacterial expression of antibody fragments, all containing one or more variable domains. These molecules include Fab-like molecules (Better et al (1988) *Science* 240, 1041); Fv molecules (Skerra et al (1988) *Science* 240, 1038); single-chain Fv (ScFv) molecules where the $V_H$ and $V_L$ partner domains are linked via a flexible oligopeptide (Bird et al (1988) *Science* 242, 423; Huston et al (1988) *Proc. Natl. Acad. Sci. USA* 85, 5879) and single domain antibodies (dAbs) comprising isolated V domains (Ward et al (1989) *Nature* 341, 544). A general review of the techniques involved in the synthesis of antibody fragments which retain their specific binding sites is to be found in Winter & Milstein (1991) *Nature* 349, 293–299.

By "ScFv molecules" we mean molecules wherein the $V_H$ and $V_L$ partner domains are linked via a flexible oligopeptide.

The advantages of using antibody fragments, rather than whole antibodies, are several-fold. The smaller size of the fragments may lead to improved pharmacological properties, such as better penetration of solid tissue. Effector functions of whole antibodies, such as complement binding, are removed. Fab, Fv, ScFv and dAb antibody fragments can all be expressed in and secreted from *E. coli*, thus allowing the facile production of large amounts of the said fragments.

Whole antibodies, and F(ab')$_2$ fragments are "bivalent". By "bivalent" we mean that the said antibodies and F(ab')$_2$ fragments have two antigen combining sites. In contrast, Fab, Fv, ScFv and dAb fragments are monovalent, having only one antigen combining sites. Fragmentation of intact immunoglobulins to produce F(ab')$_2$ fragments is disclosed by Harwood et al (1985) *Eur. J. Cancer Clin. Oncol.* 21, 1515–1522.

IgG class antibodies are preferred.

Alternatively, the entity which is recognised may or may not be antigenic but can be recognised and selectively bound to in some other way. For example, it may be a characteristic cell surface receptor such as the receptor for melanocyte-stimulating hormone (MSH) which is expressed in high numbers in melanoma cells. The cell-specific portion may then be a compound or part thereof which specifically binds to the entity in a non-immune sense, for example as a substrate or analogue thereof for a cell-surface enzyme or as a messenger.

Considerable work has already been carried out on antibodies and fragments thereof to tumour-associated antigens and antibodies or antibody fragments directed at carcino-embryonic antigen (CEA) and antibodies or their fragments directed at human chorionic gonadotrophin (hCG) can be conjugated to carboxypeptidase G2 and the resulting conjugate retains both antigen binding and catalytic function. Following intravenous injection of these conjugates they localise selectively in tumours expressing CEA or hCG respectively. Other antibodies are known to localise in tumours expressing the corresponding antigen. Such tumours may be primary and metastatic colorectal cancer (CEA) and choriocarcinoma (hCG) in human patients or other forms of cancer. Although such antibody-enzyme conjugates may also localise in some normal tissues expressing the respective antigens, antigen expression is more diffuse in normal tissues. Such antibody-enzyme conjugates may be bound to cell membranes via their respective antigens or trapped by antigen secreted into the interstitial space between cells.

Examples of tumour-associated, immune cell-associated and infection reagent-related antigens are given in Table 1.

TABLE 1

| Cell surface antigens for targeting | | |
|---|---|---|
| Antigen | Antibody | Existing uses |
| a) Tumour Associated Antigens | | |
| Carcino-embryonic Antigen | C46 (Amersham) 85A12 (Unipath) | Imaging and therapy of colon/rectum tumours. |
| Placental Alkaline Phosphatase | H17E2 (ICRF, Travers & Bodmer) | Imaging and therapy of testicular and ovarian cancers. |
| Pan Carcinoma | NR-LU-10 (NeoRx Corporation) | Imaging and therapy of various carcin- |

TABLE 1-continued

Cell surface antigens for targeting

| Antigen | Antibody | Existing uses |
|---|---|---|
| Polymorphic Epithelial Mucin (Human milk fat globule) | HMFG1 (Taylor-Papadimitriou, ICRF) | omas including small cell lung cancer. Imaging and therapy of ovarian cancer and pleural effusions. |
| β-human Chorionic Gonadotropin | W14 | Targeting of carboxypeptidase to human xenograft choriocarcinoma in nude mice (Searle et al (1981) Br. J. Cancer 44, 137–144). |
| A carbohydrate on Human Carcinomas | L6 (IgG2a)[1] | Targeting of alkaline phosphatase (Senter et al (1988) PNAS USA 85, 4842–4846. |
| CD20 Antigen on B Lymphoma (normal and neoplastic) | 1F5 (IgG2a)[2] | Targeting of alkaline phosphatase (Senter et al (1988) PNAS USA 85, 4842–4846. |

Other antigens include alphafoetoprotein, Ca-125 and prostate specific antigen b) Immune Cell Antigens

| Pan T Lymphocyte Surface Antigen (CD3) | OKT-3 (Ortho) | As anti-rejection therapy for kidney transplants. |
| B-lymphocyte Surface Antigen (CD22) | RFB4 (Janossy, Royal Free Hospital) | Immunotoxin therapy of B cell lymphoma. |
| Pan T lymphocyte Surface Antigen (CD5) | H65 (Bodmer and Knowles, ICRF; licensed to Xoma Corp., USA) | Immunotoxin treatment of acute graft versus host disease, rheumatoid arthritis. | c) Infectious Agent-Related Antigens

| Mumps virus-related | Anti-mumps polyclonal antibody | Antibody conjugated to diphtheria toxin for treatment of mumps. |
| Hepatitis B Surface Antigen | Anti HBs Ag | Immunotoxin against hepatoma. |

[1]Hellström et al (1986) Cancer Res. 46, 3917–3923
[2]Clarke et al (1985) Proc. Natl. Acad. Sci. USA 82, 1766–1770

Other tumour selective targets and suitable binding moieties are shown in Table 2.

TABLE 2

Binding moieties for tumour-selective targets and tumour-associated antigens

| Target | Binding moiety | Disease |
|---|---|---|
| Truncated EGFR | anti-EGFR mAb | Gliomas |
| Idiotypes | anti-id mAbs | B-cell lymphomas |
| EGFR (c-erbB1) | EGF, TGFα anti-EGFR mAb | Breast cancer |
| c-erbB2 | mAbs | Breast cancer |
| IL-2 receptor | IL-2 anti-Tac mAb | Lymphomas and leukaemias |
| IL-4 receptor | IL-4 | Lymphomas and leukaemias |
| IL-6 receptor | IL-6 | Lymphomas and leukaemias |
| MSH (melanocyte-stimulating hormone) receptor | α-MSH | Melanomas |
| Transferrin receptor (TR) | Transferrin anti-TR mAb | Gliomas |
| gp95/gp97 | mAbs | Melanomas |
| p-glycoprotein cells | mAbs | drug-resistant |
| cluster-1 antigen (N-CAM) | mAbs | Small cell lung carcinomas |
| cluster-w4 | mAbs | Small cell lung carcinomas |
| cluster-5A | mAbs | Small cell lung carcinomas |
| cluster-6 (LeY) | mAbs | Small cell lung carcinomas |
| PLAP (placental alkaline phosphatase) | mAbs | Some seminomas Some ovarian; some non small cell lung cancer |
| CA-125 | mAbs | Lung, ovarian |
| ESA (epithelial specific antigen) | mAbs | carcinoma |
| CD 19, 22, 37 | mAbs | B-cell lymphomas |
| 250 kDa proteoglycan p55 | mAbs | Melanoma |
| TCR-IgH fusion | mAbs | Breast cancer |
| | | Childhood T-cell leukaemia |
| Blood gp A antigen (in B or O individuals) | mAbs | Gastric and colon tumours |
| Mucin protein core | mAbs | Breast cancer |

It is preferred if the target cell-specific portion comprises an antibody or fragment or derivative thereof.

The target cell-specific portion may, however, be any compound which leads to the accumulation of the NQO2 or a said variant or fragment or fusion or derivative thereof at the site of the target cell (such as a tumour). For example, non-specific uptake of a macromolecule by a tumour is enough to deliver an appropriate level of the enzyme in an ADEPT-type of system and an adequate ratio of tumour-associated cytotoxic drug to non-tumour-associated drug can be achieved if the enzyme-macromolecule conjugate is cleared or inhibited when away from the tumour. This approach is applicable to any of the ADEPT systems described above but should perhaps be called MDEPT (macromolecule directed enzyme prodrug therapy).

The term "tumour" is to be understood as referring to all forms of neoplastic cell growth, including tumours of the lung, liver, blood cells, skin, pancreas, stomach, colon, prostate, uterus, breast, lymph glands and bladder. Solid tumours are especially suitable.

The potential advantages in using non-antibody macromolecules for this purpose are substantial. Firstly, a non-specific macromolecule may be selected that is non-immunogenic. Secondly, a macromolecule may be much less costly to produce than humanised antitumour antibody. Thirdly, it has been shown that some polymers reduce or eliminate the immunogenicity of proteins, including enzymes, attached to them (Abuchowski et al, 1977, Wileman et al, 1986, Mikolajczyk et al, 1996). Fourthly, whereas an antibody binds to only a limited range of cancers (antibodies only exist for about 60% of all malignancies), the macromolecule uptake by tumours appears to be a characteristic common to all solid cancers so far examined.

Thus, many tumours such as sarcomas for which no selective antibodies have yet been reported may be targeted using this principle.

The relatively low differential between tumour and non-tumour tissues with non-specific macromolecules is exploitable only if the level of normal tissue enzyme is inhibited, for example by using a galactosylated anti-enzyme antibody. To get the required amount of enzyme to tumour sites when the enzyme is conjugated to a non-specific macromolecule may require a greater amount of such a conjugate to be administered than would be the case with a specific antibody-enzyme conjugate, but the lower cost of the former should offset its lower efficiency.

Preferably, the macromolecule used in the invention is hydrophilic and is characterised by being soluble in body fluids and in conventional fluids for parenteral administration. Suitably, the macromolecule is biodegradable so that systemic accumulation during repeated administration is avoided. Clearly, however, it must not be degraded so fast as to fail to accumulate at the tumour site. Preferably, when conjugated to the selected enzyme, the molecular weight and size of the conjugate should exceed that of the renal threshold for urinary excretion (MW 60 000), as this helps the blood concentration to be sufficient to provide an effective blood:tumour concentration gradient. A molecular weight of up to at least 800 000 is generally suitable, for example up to 160 000. The macromolecule is preferably one which is not readily captured by the reticuloendothelial system. To make it catalytic, the macromolecule may be conjugated to one or more enzyme molecules by simple chemical methods, using bi-functional agents which do not degrade the attached enzyme. Preferably, the starting macromolecule confers reduced immunogenicity on an immunogenic enzyme to which it is conjugated.

Macromolecules that are available as sub-units and are not biodegradable may be linked by biodegradable linking units so that the non-biodegradable components are filtered through the kidneys and excreted in the urine.

Whereas some macromolecules are not known to be internalised by cells others, such as N-(2-hydroxypropyl) methylacrylamide, are internalised through more than one mechanism (Duncan et al, 1996).

Preferably, the macromolecule is polyethylene glycol (PEG). Derivatisation of proteins with polyethylene glycol has been demonstrated numerous times to increase their blood circulation lifetimes as well as decrease their antigenicity and immunogenicity.

MDEPT is described in more detail in our co-pending patent application PCT/GB97/03284 incorporated herein by reference.

Thus, a preferred embodiment for delivery of the enzyme to tumour sites is to take advantage of the leakiness of tumour capillaries and the poor lymphatic drainage of tumours. Thus, it has been shown that an enzyme conjugated to form a macromolecule, for instance by conjugation to polyethylene glycols or dextrans is selectively taken up by tumours.

The cDNA encoding human NAD(P)H:quinone reductase 2 (NQO2) is given in Jaiswal et al (1990) *Biochemistry* 29, 1899–1906 and the gene structure of the NQO2 gene is given in Jaiswal (1994) *J. Biol. Chem.* 269, 14502–14508, both of which are incorporated herein by reference and the nucleotide sequence and encoded amino acid sequence is given in FIG. 6. The skilled person can readily obtain and manipulate DNA encoding NQO2 based on the teachings contained herein using genetic engineering and recombinant DNA techniques which are well known, some of which are described in Sambrook et al (1989), "Molecular cloning, a laboratory manual", Cold Spring Harbor Laboratory Press, Cold Spring Harbor, N.Y.

A variant or fragment or fusion or derivative of NQO2 may be used in place of NQO2 with the given amino acid sequence provided that it has substantially the same activity as NQO2 towards a given prodrug. The enzyme NQO2 catalyses the conversion of, for example, the prodrug CB 1954 and prodrug analogues thereof. Thus, preferably the variant or fragment or fusion or derivative of NQO2 has substantially the same activity towards CB 1954 as does NQO2 itself. Conveniently, the said variant or fragment or fusion or derivative has at least 0.1×the $k_{cat}/K_m$ of NQO2, more preferably at least 0.5× and still more preferably at least 0.9×the $k_{cat}/K_m$ of NQO2.

Preferably, the variant or fragment or fusion or derivative of NQO2 also has substantially the same cofactor specificity. Preferably the variant or fragment or fusion or derivative of NQO2 can use nicotinamide riboside (reduced) (NRH) as a cofactor. Preferably, the variant or fragment or fusion or derivative of NQO2 binds the cofactor at least 0.1× as well as NQO2 itself, more preferably at least 0.5× as well and still more preferably at least 0.9× as well.

By a "variant" we include polypeptides in which one or more amino acids have been replaced or deleted. Typically, the variant has amino acid conservative replacements in which, for example, the following groups of amino acid may be interchanged: Gly, Ala; Val, Ile, Leu; Asp, Glu; Asn, Gln; Ser, Thr, Lys, Arg; and Phe, Tyr. Such variants may be made using the methods of protein engineering and site-directed mutagenesis. The term "variants" also includes polypeptides with insertions and deletions.

By a "fragment" we mean a portion of NQO2 provided that it retains substantially the same activity as NQO2 towards a given prodrug.

By a "fusion" we mean a fusion of NQO2 or a variant or fragment thereof to any other polypeptide, for example, in some circumstances it may be desirable to fuse NQO2 or a variant or fragment thereof to another polypeptide which can facilitate purification. This may be, for example, glutathione-S-transferase, or the well known Myc tag sequence or $His_n$ where n>4. In each case the additional polypeptide allows the fusion to be purified by affinity chromatography.

When the two portions of the compound of the first aspect of the invention are polypeptides they may be linked together by any of the conventional ways of cross-linking polypeptides, such as those generally described in O'Sullivan et al (1979) *Anal. Biochem.* 100, 100–108. For example, an antibody portion may be enriched with thiol groups and the enzyme portion reacted with a bifunctional agent capable of reacting with those thiol groups, for example the N-hydroxysuccinimide ester of iodoacetic acid (NHIA) or N-succinimidyl-3-(2-pyridyldithio)propionate (SPDP). Amide and thioether bonds, for example achieved with m-maleimidobenzoyl-N-hydroxysuccinimide ester, are generally more stable in vivo than disulphide bonds.

It may not be necessary for the whole NQO2 to be present in the compound of the first aspect of the invention but, of course, the catalytic portion must be present.

Alternatively, the compound may be produced as a fusion compound by recombinant DNA techniques whereby a length of DNA comprises respective regions encoding the two portions of the compound of the invention either adjacent to one another or separated by a region encoding a linker peptide which does not destroy the desired properties of the compound. Conceivably, the two portions of the compound may overlap wholly or partly. The antibody (or other polypeptide portion which targets a cell) component of the fusion must be represented by at least one binding site. Examples of the construction of antibody (or anti-body fragment)-enzyme fusions are disclosed by Neuberger et al (1984) *Nature* 312, 604.

The DNA is then expressed in a suitable host to produce a polypeptide comprising the compound of this aspect of the invention. Thus, the DNA encoding the polypeptide constituting the compound of this aspect of the invention may be used in accordance with known techniques, appropriately modified in view of the teachings contained herein, to construct an expression vector, which is then used to transform an appropriate host cell for the expression and production of the polypeptide of the invention. Such techniques include those disclosed in U.S. Pat. No. 4,440,859 issued 3 Apr. 1984 to Rutter et al, U.S. Pat. No. 4,530,901 issued 23 Jul. 1985 to Weissman, U.S. Pat. No. 4,582,800 issued 15 Apr. 1986 to Crowl, U.S. Pat. No. 4,677,063 issued 30 Jun. 1987 to Mark et al, U.S. Pat. No. 4,678,751 issued 7 Jul. 1987 to Goeddel, U.S. Pat. No. 4,704,362 issued 3 Nov. 1987 to Itakura et al, U.S. Pat. No. 4,710,463 issued 1 Dec. 1987 to Murray, U.S. Pat. No. 4,757,006 issued 12 Jul. 1988 to Toole, Jr. et al, U.S. Pat. No. 4,766,075 issued 23 Aug. 1988 to Goeddel et al and U.S. Pat. No. 4,810,648 issued 7 Mar. 1989 to Stalker, all of which are incorporated herein by reference.

The DNA encoding the polypeptide constituting the compound of this aspect of the invention may be joined to a wide variety of other DNA sequences for introduction into an appropriate host. The companion DNA will depend upon the nature of the host, the manner of the introduction of the DNA into the host, and whether episomal maintenance or integration is desired.

Generally, the DNA is inserted into an expression vector, such as a plasmid, in proper orientation and correct reading frame for expression. If necessary, the DNA may be linked to the appropriate transcriptional and translational regulatory control nucleotide sequences recognised by the desired host, although such controls are generally available in the expression vector. The vector is then introduced into the host through standard techniques. Generally, not all of the hosts will be transformed by the vector. Therefore, it will be necessary to select for transformed host cells. One selection technique involves incorporating into the expression vector a DNA sequence, with any necessary control elements, that codes for a selectable trait in the transformed cell, such as antibiotic resistance. Alternatively, the gene for such selectable trait can be on another vector, which is used to co-transform the desired host cell.

Host cells that have been transformed by the recombinant DNA of the invention are then cultured for a sufficient time and under appropriate conditions known to those skilled in the art in view of the teachings disclosed herein to permit the expression of the polypeptide. which can then be recovered.

Many expression systems are known, including bacteria (for example *E. coli* and *Bacillus subtilis*), yeasts (for example *Saccharomyces cerevisiae*), filamentous fungi (for example *Aspergillus*), plant cells, animal cells and insect cells.

The vectors include a procaryotic replicon, such as the ColE1 ori, for propagation in a procaryote, even if the vector is to be used for expression in other, non-procaryotic, cell types. The vectors can also include an appropriate promoter such as a procaryotic promoter capable of directing the expression (transcription and translation) of the genes in a bacterial host cell, such as *E. coli*, transformed therewith.

A promoter is an expression control element formed by a DNA sequence that permits binding of RNA polymerase and transcription to occur. Promoter sequences compatible with exemplary bacterial hosts are typically provided in plasmid vectors containing convenient restriction sites for insertion of a DNA segment of the present invention.

Typical procaryotic vector plasmids are pUC18, pUC19, pBR322 and pBR329 available from Biorad Laboratories, (Richmond, Calif., USA) and pTrc99A and pKK223-3 available from Pharmacia, Piscataway, N.J., USA.

A typical mammalian cell vector plasmid is pSVL available from Pharmacia, Piscataway, N.J., USA. This vector uses the SV40 late promoter to drive expression of cloned genes, the highest level of expression being found in T antigen-producing cells, such as COS-1 cells.

An example of an inducible mammalian expression vector is pMSG, also available from Pharmacia. This vector uses the glucocorticoid-inducible promoter of the mouse mammary tumour virus long terminal repeat to drive expression of the cloned gene.

Useful yeast plasmid vectors are pRS403–406 and pRS413–416 and are generally available from Stratagene Cloning Systems, La Jolla, Calif. 92037, USA. Plasmids pRS403, pRS404, pRS405 and pRS406 are Yeast Integrating plasmids (YIps) and incorporate the yeast selectable markers his3, trp1, leu2 and ura3. Plasmids pRS413–416 are Yeast Centromere plasmids (YCps).

A variety of methods have been developed to operatively link DNA to vectors via complementary cohesive termini. For instance, complementary homopolymer tracts can be added to the DNA segment to be inserted to the vector DNA. The vector and DNA segment are then joined by hydrogen bonding between the complementary homopolymeric tails to form recombinant DNA molecules.

Synthetic linkers containing one or more restriction sites provide an alternative method of joining the DNA segment to vectors. The DNA segment, generated by endonuclease restriction digestion as described earlier, is treated with bacteriophage T4 DNA polymerase or *E. coli* DNA polymerase I. enzymes that remove protruding, 3'-single-stranded termini with their 3'-5'-exonucleolytic activities, and fill in recessed 3'-ends with their polymerizing activities.

The combination of these activities therefore generates blunt-ended DNA segments. The blunt-ended segments are then incubated with a large molar excess of linker molecules in the presence of an enzyme that is able to catalyze the ligation of blunt-ended DNA molecules, such as bacteriophage T4 DNA ligase. Thus, the products of the reaction are DNA segments carrying polymeric linker sequences at their ends. These DNA segments are then cleaved with the appropriate restriction enzyme and ligated to an expression vector that has been cleaved with an enzyme that produces termini compatible with those of the DNA segment.

Synthetic linkers containing a variety of restriction endonuclease sites are commercially available from a number of sources including International Biotechnologies Inc, New Haven, Conn., USA.

A desirable way to modify the DNA encoding the polypeptide of this aspect of the invention is to use the polymerase chain reaction as disclosed by Saiki et al (1988) *Science* 239, 487–491.

In this method the DNA to be enzymatically amplified is flanked by two specific oligonucleotide primers which themselves become incorporated into the amplified DNA. The said specific primers may contain restriction endonuclease recognition sites which can be used for cloning into expression vectors using methods known in the art.

Exemplary genera of yeast contemplated to be useful in the practice of the present invention are *Pichia, Saccharomyces, Kluyveromyces, Candida, Torulopsis, Hansenula, Schizosaccharomyces, Citeromyces, Pachysolen, Debaromyces, Metscliunikowia, Rhodosporidium, Leucosporidium, Botryoascus, Sporidiobolus, Endomycopsis*, and the like.

Preferred genera are those selected from the group consisting of *Pichia*, *Saccharomyces*, *Kluyveromyces*, *Yarrowia* and *Hansenula*. Examples of *Saccharomyces* are *Saccharomyces cerevisiae*, *Saccharomyces italicus* and *Saccharomyces rouxii*. Examples of *Kluyveromyces* are *Kluyveromyces fragilis* and *Kluyveromyces lactis*. Examples of *Hansenula* are *Hansenula polymorpha*, *Hansenula anomala* and *Hansenula capsulata*. *Yarrowia lipolytica* is an example of a suitable *Yarrowia* species.

Methods for the transformation of *S. cerevisiae* are taught generally in EP 251 744, EP 258 067 and WO 90/01063, all of which are incorporated herein by reference.

Suitable promoters for *S. cerevisiae* include those associated with the PGK1 gene, GAL1 or GAL10 genes, CYC1, PHO5, TRP1, ADH1, ADH2, the genes for glyceraldehyde-3-phosphate dehydrogenase, hexokinase, pyruvate decarboxylase, phosphofructokinase. triose phosphate isomerase, phosphoglucose isomerase, glucokinase, α-mating factor pheromone, a-mating factor pheromone, the PRB1 promoter, the GUT2 promoter, and hybrid promoters involving hybrids of parts of 5' regulatory regions with parts of 5' regulatory regions of other promoters or with upstream activation sites (eg the promoter of EP-A-258 067).

The transcription termination signal is preferably the 3' flanking sequence of a eukaryotic gene which contains proper signals for transcription termination and polyadenylation. Suitable 3' flanking sequences may, for example, be those of the gene naturally linked to the expression control sequence used, ie may correspond to the promoter. Alternatively, they may be different in which case the termination signal of the *S. cerevisiae* AHD1 gene is preferred.

By "polynucleotide encoding said NQO2 or said variant or fragment or fusion or derivative" we include any such polynucleotide. The polynucleotide may be RNA or DNA; preferably it is DNA.

It will be appreciated that when the compound of the first aspect of the invention comprises a polynucleotide encoding human NQO2 or a polynucleotide encoding a variant or fragment or fusion or derivative thereof which has substantially the same activity as NQO2 towards a given prodrug the target cell-specific portion of the compound is one which is adapted to deliver the polynucleotide (genetic construct) to the target cell.

Preferably, the genetic construct is adapted for delivery to a cell, preferably a human cell. More preferably, the genetic construct is adapted for delivery to a cell in an animal body, more preferably a mammalian body; most preferably it is adapted for delivery to a cell in a human body.

Means and methods of introducing a genetic construct into a cell in an animal body are known in the art. For example, the constructs of the invention may be introduced into the tumour cells by any convenient method, for example methods involving retroviruses, so that the construct is inserted into the genome of the tumour cell. For example, in Kuriyama et al (1991) *Cell Struc. and Func.* 16, 503–510 purified retroviruses are administered. Retroviruses provide a potential means of selectively infecting cancer cells because they can only integrate into the genome of dividing cells; most normal cells surrounding cancers are in a quiescent, non-receptive stage of cell growth or, at least, are dividing much less rapidly than the tumour cells. Retroviral DNA constructs which contain a suitable promoter segment and a polynucleotide encoding NQO2 or a variant or fragment or fusion or derivative as defined may be made using methods well known in the art. To produce active retrovirus from such a construct it is usual to use an ecotropic psi2 packaging cell line grown in Dulbecco's modified Eagle's medium (DMEM) containing 10% foetal calf serum (FCS). Transfection of the cell line is conveniently by calcium phosphate co-precipitation, and stable transformants are selected by addition of G418 to a final concentration of 1 mg/ml (assuming the retroviral construct contains a neo$^R$ gene). Independent colonies are isolated and expanded and the culture supernatant removed, filtered through a 0.45 µm pore-size filter and stored at −70°. For the introduction of the retrovirus into the tumour cells, it is convenient to inject directly retroviral supernatant to which 10 µg/ml Polybrene has been added. For tumours exceeding 10 mm in diameter it is appropriate to inject between 0.1 ml and 1 ml of retroviral supernatant; preferably 0.5 ml.

Alternatively, as described in Culver et at (1992) *Science* 256, 1550–1552, cells which produce retroviruses are injected into the tumour. The retrovirus-producing cells so introduced are engineered to actively produce retroviral vector particles so that continuous productions of the vector occurred within the tumour mass in situ. Thus, proliferating tumour cells can be successfully transduced in vivo if mixed with retroviral vector-producing cells.

Targeted retroviruses are also available for use in the invention; for example, sequences conferring specific binding affinities may be engineered into preexisting viral env genes (see Miller & Vile (1995) *Faseb J.* 9, 190–199 for a review of this and other targeted vectors for gene therapy).

Other methods involve simple delivery of the construct into the cell for expression therein either for a limited time or, following integration into the genome, for a longer time. An example of the latter approach includes (preferably tumour-cell-targeted) liposomes (Nassander et al (1992) *Cancer Res.* 52, 646–653).

Immunoliposomes (antibody-directed liposomes) are especially useful in targeting to cancer cell types which over-express a cell surface protein for which antibodies are available (see Table for examples). For the preparation of immuno-liposomes MPB-PE (N-[4-(p-maleimidophenyl)-butyryl]-phosphatidylethanolamine) is synthesised according to the method of Martin & Papahadjopoulos (1982) *J. Biol. Chem.* 257, 286–288. MPB-PE is incorporated into the liposomal bilayers to allow a covalent coupling of the antibody, or fragment thereof, to the liposomal surface. The liposome is conveniently loaded with the DNA or other genetic construct of the invention for delivery to the target cells, for example, by forming the said liposomes in a solution of the DNA or other genetic construct, followed by sequential extrusion through polycarbonate membrane filters with 0.6 µm and 0.2 µm pore size under nitrogen pressures up to 0.8 MPa. After extrusion, entrapped DNA construct is separated from free DNA construct by ultracentrifugation at 80 000×g for 45 min. Freshly prepared MPB-PE-liposomes in deoxygenated buffer are mixed with freshly prepared antibody (or fragment thereof) and the coupling reactions are carried out in a nitrogen atmosphere at 4° C. under constant end over end rotation overnight. The immunoliposomes are separated from unconjugated antibodies by ultracentrifugation at 80 000×g for 45 min. Immunoliposomes may be injected intraperitoneally or directly into the tumour. Other methods of delivery include adenoviruses carrying external DNA via an antibody-polylysine bridge (see Curiel *Prog. Med. Virol.* 40, 1–18) and transferrin-polyeation conjugates as carriers (Wagner et al (1990) *Proc. Natl. Acad. Sci. USA* 87, 3410–3414). In the first of these methods a polycation-antibody complex is formed with the DNA construct or other genetic construct of the invention, wherein the antibody is specific for either wild-type adenovirus or a variant adenovirus in which a new epitope has been introduced which binds the antibody. The polycation moiety binds the DNA via electrostatic interactions with the phosphate backbone. It is preferred if the polycation is polylysine.

The DNA may also be delivered by adenovirus wherein it is present within the adenovirus particle, for example, as described below.

In the second of these methods, a high-efficiency nucleic acid delivery system that uses receptor-mediated endocytosis to carry DNA macromolecules into cells is employed. This is accomplished by conjugating the iron-transport protein transferrin to polycations that bind nucleic acids. Human transferrin, or the chicken homologue conalbumin, or combinations thereof is covalently linked to the small DNA-binding protein protamine or to polylysines of various sizes through a disulfide linkage. These modified transferrin molecules maintain their ability to bind their cognate receptor and to mediate efficient iron transport into the cell. The transferrin-polycation molecules form electrophoretically stable complexes with DNA constructs or other genetic constructs of the invention independent of nucleic acid size (from short oligonucleotides to DNA of 21 kilobase pairs). When complexes of transferrin-polycation and the DNA constructs or other genetic constructs of the invention are supplied to the tumour cells, a high level of expression from the construct in the cells is expected.

High-efficiency receptor-mediated delivery of the DNA constructs or other genetic constructs of the invention using the endosome-disruption activity of defective or chemically inactivated adenovirus particles produced by the methods of Cotten et al (1992) *Proc. Natl. Acad. Sci. USA* 89, 6094–6098 may also be used. This approach appears to rely on the fact that adenoviruses are adapted to allow release of their DNA from an endosome without passage through the lysosome, and in the presence of, for example transferrin linked to the DNA construct or other genetic construct of the invention, the construct is taken up by the cell by the same route as the adenovirus particle.

This approach has the advantages that there is no need to use complex retroviral constructs; there is no permanent modification of the genome as occurs with retroviral infection; and the targeted expression system is coupled with a targeted delivery system, thus reducing toxicity to other cell types.

It may be desirable to locally perfuse a tumour with the suitable delivery vehicle comprising the genetic construct for a period of time; additionally or alternatively the delivery vehicle or genetic construct can be injected directly into accessible tumours.

It will be appreciated that "naked DNA" and DNA complexed with cationic and neutral lipids may also be useful in introducing the DNA of the invention into cells of the patient to be treated. Non-viral approaches to gene therapy are described in Ledley (1995) *Human Gene Therapy* 6, 1129–1144.

Thus, it will be appreciated that a further aspect of the invention provides a composition comprising genetic construct as defined in the invention and means for introducing said genetic construct into a cell, preferably the cell of an animal body.

Alternative targeted delivery systems are also known such as the modified adenovirus system described in WO 94/10323 wherein, typically, the DNA is carried within the adenovirus, or adenovirus-like, particle. Michael et al (1995) *Gene Therapy* 2, 660–668 describes modification of adenovirus to add a cell-selective moiety into a fibre protein. Mutant adenoviruses which replicate selectively in p53-deficient human tumour cells, such as those described in Bischoff et al (1996) *Science* 274, 373–376 are also useful for delivering the genetic construct of the invention to a cell. Thus, it will be appreciated that a further aspect of the invention provides a virus or virus-like particle comprising a genetic construct of the invention. Other suitable viruses or virus-like particles include HSV, AAV, vaccinia and parvovirus.

It will be appreciated that in the first aspect of the invention the polynucleotide need not be one which has a target cell-specific promoter to drive the expression of NQO2 or said variant or fragment or fusion or derivative thereof since the compound comprises a target cell-specific portion as described above for targeting the polynucleotide to the target cell. However, it may be advantageous if the polynucleotide comprises a target cell-specific promoter operably linked to a polynucleotide encoding human NAD (P)H:quinone reductase 2 (NQO2) or a variant or fragment or fusion or derivative thereof which has substantially the same activity as NQO2 towards a given prodrug.

It will be further appreciated that target cell-specific expression of NQO2 or the said variants, fragments, fusions or derivatives may be achieved using a polynucleotide or genetic construct comprising a target cell-specific promoter whether or not the polynucleotide or genetic construct is comprised in a compound of the first aspect of the invention.

Thus, a second aspect of the invention provides a recombinant polynucleotide comprising a target cell-specific promoter operably linked to a polynucleotide encoding human NAD(P)H:quinone reductase 2 (NQO2) or a variant or fragment or fusion or derivative thereof which has substantially the same activity as NQO2 towards a given prodrug.

Preferably the target cell-specific promoter is a tumour cell-specific promoter.

Useful genetic elements which are target cell-specific promoters are given below but new ones are being discovered all of the time which will be useful in this embodiment of the invention.

The tyrosinase and TRP-1 genes both encode proteins which play key roles in the synthesis of the pigment melanin, a specific product of melanocytic cells. The 5' ends of the tyrosinase and tyrosinase-related protein (TRP-1) genes confer tissue specificity of expression on genes cloned downstream of these promoter elements.

The 5' sequences of these genes are described in Bradl, M. et al (1991) *Proc. Natl. Acad. Sci. USA* 88, 164–168 and Jackson, I. J. et al (1991) *Nucleic Acids Res.* 19, 3799–3804.

Prostate-specific antigen (PSA) is one of the major protein constituents of the human prostate secretion. It has become a useful marker for the detection and monitoring of prostate cancer. The gene encoding PSA and its promoter region which directs the prostate-specific expression of PSA have been described (Lundwall (1989) *Biochem. Biophys. Res. Comm.* 161, 1151–1159; Riegman et al (1989) *Biochem. Biophys. Res. Comm.* 159, 95–102; Brawer (1991) *Acta Oncol.* 30, 161–168).

Carcinoembryonic antigen (CEA) is a widely used tumour marker, especially in the surveillance of colonic cancer patients. Although CEA is also present in some normal tissues, it is apparently expressed at higher levels in tumorous tissues than in corresponding normal tissues. The complete gene encoding CEA has been cloned and its promoter region analysed. A CEA gene promoter construct, containing approximately 400 nucleotides upstream from the translational start, showed nine times higher activity in the adenocarcinoma cell line SW303, compared with the HeLa cell line. This indicates that cis-acting sequences which convey cell type specific expression are contained within this region (Schrewe et al (1990) *Mol. Cell. Biol.* 10, 2738–2748).

The mucin gene, MUC1, contains 5' flanking sequences which are able to direct expression selectively in breast and pancreatic cell lines, but not in non-epithelial cell lines as taught in WO 91/09867.

The alpha-fetoprotein (AFP) enhancer may be useful to drive pancreatic tumour-selective expression (Su et al (1996) *Hum. Gene Ther.* 7, 463–470).

The genetic constructs of the invention can be prepared using methods well known in the art.

A third aspect of the invention provides a therapeutic system (or, as it may be termed, a kit of parts) comprising a compound of the first aspect of the invention or a polynucleotide of the second aspect of the invention and a prodrug which is converted to a substantially cytotoxic drug by the action of NQO2.

Preferably the prodrug is CB 1954 or an analogue thereof; most preferably the prodrug is CB 1954.

Analogues of CB1954 are suitably defined as molecules which retain the essential structural features of CB1954 ie a benzene ring containing an aziridine ring, two NO$_2$ groups and another substituent R but which differ in either the relative orientation of the substituents and/or in the nature of R. A number of analogues have been disclosed in Khan A. H. and Ross W. C. J. (1969) *Chem. Biol. Interact.* 1, 27–47 and in Khan A. H. and Ross W. C. J. (1971) *Chem. Biol. Interact.* 4, 11–22, both of which are incorporated herein by reference and in particular the details of the analogues of CB1954 are included in this description.

Preferably the therapeutic system further comprises NRH or an analogue thereof which is able to pass reducing equivalents to NQO2. Suitable analogues include the reduced form of 1-methylnicotinamide and others which are also described in Friedlos et al (1992b) and Knox et al (1995), both of which are incorporated herein by reference.

A fourth aspect of the invention provides a method of treating a patient with a target cell to be destroyed the method comprising (a) administering to the patient a compound of the first aspect of the invention or a recombinant polynucleotide of the second aspect of the invention; (b) allowing the NQO2 or a variant or fragment or fusion or derivative thereof to localize at, or be expressed in, the target cell; and (c) administering a prodrug which is converted to a substantially cytotoxic drug by the action of NQO2. It is particularly preferred if NRH or another suitable cofactor of NQO2 is administered to the patient. Another suitable cofactor of NQO2 includes analogues of NRH which are able to pass reducing equivalents to NQO2 and includes molecules which are able to bind NQO2 and pass reducing equivalents to NQO2 substantially as NRH. The administration of the cofactor may be before or after or at the same time as administration of the prodrug.

It is particularly preferred if NRH or an analogue thereof is administered before the prodrug.

Thus, the method is useful in destroying a target cell in a host (eg patient).

Preferably, the patient to be treated has a tumour.

The prodrug may be any suitable prodrug as described above.

Preferably the prodrug is CB 1954 or an analogue thereof.

Preferably, when the compound is one comprising a target cell-specific portion and human NAD(P)H:quinone reductase 2 (NQO2) or a variant or fragment or fusion or derivative thereof which has substantially the same activity as NQO2 towards a given prodrug, the compound is administered and, once there is an optimum balance between the target cell to normal cell ratio of the compound and the absolute level of compound associated with the target, the prodrug which is converted to a substantially cytotoxic drug by the action of NQO2 is administered. The interval between the administration of the compound and the prodrug will depend on the target cell localisation characteristics of the particular compound, but typically it will be between 6 and 48 hours.

Suitably, prodrug administration commences as soon as the plasma activity of enzyme and, by inference, the activity in normal tissues, is insufficient to catalyse enough prodrug to cause toxicity.

Thus, in a preferred embodiment, NQO2 is conjugated to a monoclonal antibody directed at a tumour-associated antigen so as to localise at tumour sites and CB1954 given when the enzyme has cleared from blood and normal tissues. As discussed above, it is particularly preferred if NRH or another suitable cofactor of NQO2 is administered to the patient. Preferably, NRH or an analogue thereof is administered before the prodrug.

Preferably, when the compound is one comprising a target cell-specific portion and a polynucleotide encoding human NAD(P)H:quinone reductase 2 (NQO2) or a variant or fragment or fusion or derivative thereof which has substantially the same activity as NQO2 towards a given prodrug, the compound is administered and, once the NQO2 or a said variant or derivative or fusion or fragment thereof is expressed in the target cell to a useful extent, the prodrug is administered. As discussed above it is particularly preferred if NRH or another suitable cofactor of NQO2 is administered to the patient. Preferably, NRH or an analogue thereof is administered before the prodrug.

In this embodiment, the interval between the administration of the compound and the prodrug will depend on the target cell localisation characteristics of the particular compound but also on the expression characteristics of the polynucleotide in the particular target cell.

Preferably, then a recombinant polynucleotide of the second aspect of the invention is administered in the method of treatment of the invention, the recombinant polynucleotide is expressed in the target cells to produce NQO2 or a said variant or derivative or fragment or fusion thereof and when the expression is at a useful level, the prodrug is administered. As discussed above, it is particularly preferred if NRH or another suitable cofactor of NQO2 is administered to the patient. Preferably, NRH or an analogue thereof is administered before the prodrug.

Thus, the cytotoxic drug is released in relatively high concentration at the target or tumour site but not at non-target or non-tumour sites.

It will be appreciated that it is not necessary for the compound of the invention to locate to, or the polynucleotide of the invention to be expressed in, all target cells but that the compound should locate to, or the polynucleotide be expressed in, sufficient target cells to have a desirable effect upon administration of the prodrug.

At least with the ADEPT-type embodiment of the invention it may be advantageous to make use of a modification of the system which allows for improved target cell selectivity (especially tumour cell selectivity) by clearing antibody-enzyme conjugates from the blood.

The principle of this improvement is described in detail in WO 89/10140, incorporated herein by reference. Thus, clearance of residual enzyme activity from blood and normal tissues can be accelerated thereby maximising the tumour to normal tissue ratio of enzyme. Accelerated clearance has been achieved, for example, by means of a monoclonal antibody directed at any part of the antibody-enzyme conjugate but is especially effective when the anti-enzyme antibody inactivates the enzyme. To avoid the anti-enzyme antibody inactivating enzyme at tumour sites it can be galactosylated which results in rapid removal of the anti-enzyme-enzyme-antibody complex from the blood by galactose receptors in hepatocytes. This has been described in WO 89/10140 and in Sharma et al, 1990.

At least with the ADEPT- and MDEPT-type embodiments of the present invention it may be advantageous to make use of a modification of the system which allows for improved target cell selectivity (especially tumour cell selectivity) by using inhibitors of NQO2. For example, flavones are inhibitors of NQO2. Quercetin (3,5,7,3',4'-pentahydroxyflavone) is the most potent inhibitor tested so far. It is a competitive inhibitor with respect to NRH ($K_1$=27 nm), and so may be particularly useful. The principle of this improvement is described in detail in our co-pending patent application PCT/GB96/03000, incorporated herein by reference. Thus, an alternative to the use of a second monoclonal antibody for clearance of enzyme from blood and normal tissues is to employ a small molecule which complements the active site of the enzyme but is not a substrate and is sterically bound in the site. Such a molecule has to be administered at a dose level to inactivate enzyme in blood and normal tissues but at a dose level insufficient to inactivate the higher concentration of enzyme in tumour tissues.

At least in the ADEPT-type embodiment of the method of the invention it may be advantageous if the compound is taken up by the target cell such that the enzyme is present within the target cell. The principles of this improvement are described in our co-pending patent application PCT/GB96/03254, incorporated herein by reference.

The methods of treatment of the fourth aspect of the invention allow for the NQO2 or said derivative or fragment or variant or fusion to be present either within the target cell or outside the target cell. For example, in the embodiments wherein a polypeptide version of NQO2 are administered to the patient the polypeptide may locate either within the target cell (for example, by using the ADEPT system with internalising antibodies) or it may locate outside the target cell (for example, by using the ADEPT system with antibodies which remain substantially outside the target cell).

Similarly, in the embodiments wherein a polynucleotide encoding NQO2 are administered to the patient the polynucleotide may express NQO2 which is retained within the target cell or it may express NQO2 outside of, but associated with, the target cell. External expression of the enzyme may be achieved by linking it to a signal sequence which directs the enzyme to the surface of a mammalian cell. This will normally be a mammalian signal sequence or a derivative thereof which retains the ability to direct the enzyme to the cell surface. Suitable signal sequences include those found in transmembrane receptor tyrosine kinases such as c-erbB2 signal sequence, the sequence of which is published in Coussens et al (1985) Science 230, 1132–1139, incorporated herein by reference.

In those embodiments of the method where NQO2 is located outside the target cell, but nevertheless associated with the target cell, it will be appreciated that cosubstrate need not be permeable to the cell membrane and this is a preferred property of the cosubstrate in this embodiment since there will be no reduction of the prodrug by endogenous, intracellular NQO2. In this embodiment it is preferred if the prodrug is substantially unable to permeate the cell membrane although it may do so. However, it is believed that the cytotoxic drug should be able to penetrate the cell because it is generally believed that its cytotoxic effect is due to its reactivity within the cell.

It is preferred if the system of the third aspect of the invention further comprises a cosubstrate for NQO2 which is substantially permeable to the target cell membrane.

It is also preferred if the method of the fourth aspect of the invention further comprises administering to the patient an effective amount of a cosubstrate for NQO2 which can substantially permeate to the target cell membrane.

It is preferred if the cosubstrate is NRH or an analogue thereof especially one which can substantially permeate a cell membrane. Suitable analogues include the reduced form of 1-methylnicotinamide and others which are also described in Friedlos et al (1992b) and Knox et al (1995), both of which are incorporated herein by reference.

Thus, it will be seen that the compound of the first aspect of the invention and the recombinant polynucleotide of the second aspect of the invention are useful in medicine and that they are therefore packaged and presented for use in medicine.

The invention also provides the use of a compound of the first aspect of the invention, or a polynucleotide of the second aspect of the invention, in the manufacture of a medicament for treating a target cell to be destroyed. Preferably the patient has been, is being or will be administered a prodrug which is converted to a substantially cytotoxic drug by action of NQO2.

The invention also provides the use of a prodrug which is converted to a substantially cytotoxic drug by the action of NQO2 in the manufacture of a medicament for treating a patient with a target cell to be destroyed wherein the patient has been, is being or will be administered a compound according to the first aspect of the invention, or a polynucleotide according to the second aspect of the invention.

The invention also provides the use of NRH or an analogue thereof which can pass reducing equivalents to NQO2 in the manufacture of a medicament for treating a patient with a target cell to be destroyed wherein the patient has been, is being or will be a compound according to the first aspect of the invention, or a polynucleotide according to the second aspect of the invention and a prodrug which is converted to a substantially cytotoxic drug by the action of NQO2.

A fifth aspect of the invention provides a method of treating a human patient with a target cell to be destroyed wherein the target cell expresses NQO2 the method comprising administering to the patient a prodrug which is converted to a substantially cytotoxic drug by the action of NQO2 and nicotinamide riboside (reduced) (NRH) or an analogue thereof which can pass reducing equivalents to NQO2.

Preferably the target cell expresses NQO2 naturally (for example by virtue of the disease state) but it may be a target cell which has been induced to produce NQO2 or which expresses NQO2 by virtue of induction or manipulation of the cell.

The NRH analogues are those as described above in relation to the previous aspects of the invention.

The prodrugs are those as described above in relation to the previous aspects of the invention. It is particularly preferred if the prodrug is CB1954 or an analogue thereof.

It is particularly preferred if NRH or an analogue thereof which is substantially able to permeate the target cell membrane is used in the method of the fifth aspect of the invention.

Preferably the target cell is a tumour cell. It is particularly preferred to use the method of treatment for tumours which show an elevated level of NQO2 compared to non-tumour tissue.

Co-administration of CB 1954 with the co-factor NRH provides a basis for activation of CB 1954 at intracellular sites where NQO2 is expressed. Present indications are that the enzyme is highly expressed in colorectal cancers. It may also be expressed in some normal tissues and, if so, activation in normal tissues may be dose limiting.

Thus, it is particularly preferred to treat colorectal cancers with the method of the invention.

According to the method of the invention a prodrug and a co-substrate is administered to a tumour-bearing mammalian host. The prodrug, that is much less cytotoxic to tumour cells than the active drug, is converted to its active form by the enzyme human NAD(P)H:quinone oxidoreductase 2 (NQO2) only in the presence of the co-substrate. Prodrugs that are useful in the method of this invention include, but are not limited to, CB 1954 (5-(aziridin-1-yl)-2,4-dinitrobenzamide). Co-substrates that are useful in the method of this invention include, but are not limited to, NRH (nicotinamide mononucleoside-reduced (dihydronicotinamide riboside)) (FIG. 2). It is appreciated that both the prodrug and co-substrate should be substantially capable of permeating the cell membrane. NADH and NMNH are substantially impermeable to cell membranes. However, it will be appreciated that "by administering NRH or an analogue thereof" in relation to this and previous aspects of the invention we include administering a compound which is converted within the body of the patient to NRH or an analogue thereof. It will be appreciated that a further embodiment includes the possibility of administering to the patient a precursor of NRH or an analogue thereof and means for converting the precursor to NRH or an analogue thereof.

According to a preferred embodiment of this invention endogenous NQO2 is used to activate CB 1954 in the presence of NRH (FIG. 3). Using in vitro enzyme assays it is demonstrated that CB 1954 is reduced to its 4-hydroxylamine derivative (5-(aziridin-1-yl)-4-hydroxylamino-2-nitrobenzamide). This reduction is much greater than that by either human or rat DT-diaphorase and is not readily catalysed by either of the biogenic co-substrates, NADH or NADPH.

The method of the fifth aspect of the invention is particularly suited for the treatment of a patient with target cells to be destroyed wherein the target cells express NQO2. Thus, in a particularly preferred embodiment it is determined whether the target cells express NQO2 prior to administration of the prodrug or NRH or an analogue. This determination can be achieved, for example, by measuring NQO2 levels in a sample comprising the target cell. This may be achieved enzymatically or by using probes selective for the NQO2 polypeptide or mRNA. Conveniently, this can be achieved using the techniques commonly referred to as western and northern blotting, respectively. In the case of the polypeptide the probe may be a mono- or polyclonal antibody raised against the NQO2 protein or a fragment thereof. Such antibodies could also be used to identify NQO2 in tissue sections by using immunocytochemistry and related techniques. Probes against mRNA will be oligonucleotides or DNA fragments complementary to partial sequences of the NQO2 mRNA sequence. Although these methods are preferred, other methods may be used to detect and quantify NQO2 polypeptide or mRNA levels in a target cell or tissue.

The invention therefore also includes a therapeutic system comprising a prodrug which is converted to a substantially cytotoxic drug by the action of NQO2 and nicotinamide riboside (reduced) (NRH) or an analogue thereof which can pass reducing equivalents to NQO2. It is preferred if the system further comprises means for determining whether the target cell expresses NQO2.

The invention also includes nicotinamide riboside (reduced) (NRH) or an analogue thereof which can pass reducing equivalents to NQO2 for use in medicine, use of nicotinamide riboside (reduced) (NRH) or an analogue thereof which can pass reducing equivalents to NQO2 in the manufacture of a medicament for treating a human patient with a target cell to be destroyed, and use of a prodrug which is converted to a substantially cytotoxic drug by the action of NQO2 in the manufacture of a medicament for treating a human patient with a target cell to be destroyed wherein the patient has been, is being or will be administered NRH or an analogue thereof which can pass reducing equivalents to NQO2.

By "NRH or an analogue thereof which is able to pass reducing equivalents to NQO2" we include, as is mentioned above, the reduced form of 1-methylnicotinamide and others which are also described in Friedlos et al (1992b) and Knox et al (1995). The $k_{cat}$ for NQO2/NRH is 360 min$^{-1}$ using CB1954 as an electron acceptor. A cosubstrate (ie an analogue of NRH which is able to pass reducing equivalents to NQO2) is a compound that can act as a cosubstrate for NQO2 so that the enzyme can reduce CB1954 to its 4-hydroxylamine derivative with a $k_{cat}$>50 min$^{-1}$. For the avoidance of doubt, an "analogue of NRH which is able to pass reducing equivalents to NQO2" need not necessarily be a structural analogue of NRH but is a functional analogue of NRH in the sense that it can pass reducing equivalents to NQO2. For the avoidance of doubt NADH and NADPH are not cosubstrates for NQO2.

Certain cosubstrates (analogues of NRH) have the structure:

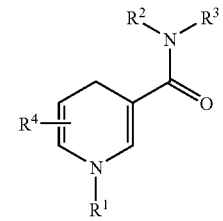

where $R^1$ is alkyl, aryl, substituted alkyl, substituted aryl, $CONR^aR^b$ (where $R^a$ and $R^b$ are independently H, alkyl, or substituted alkyl), and $R^2$ and $R^3$ are independently H, alkyl, or substituted alkyl. $R^4$ is any of H, alkyl, substituted alkyl, halogen, CN, COOH, $CONH_2$ or OH. Preferably, $R^4$ is H.

Whether or not compounds of this structure act as cosubstrates of NQO2 can readily be determined by methods as disclosed herein.

Preferably, $R^2$ and $R^3$ are H. Preferably $R^1$ is alkyl or substituted alkyl. Thus, it is preferred if the cosubstrate has the general structure

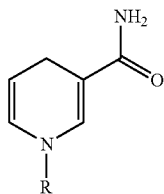

where R is alkyl or substituted alkyl.

It is preferred that the alkyl group is $C_1$ to $C_6$ alkyl, and it is further preferred that the alkyl group is a linear alkyl group.

By "substituted alkyl" we include substitution by OH, halogen, CN, COOH and $CONH_2$.

We have synthesised the following compounds:
1: $R = -CH_2CH_2CH_2SO_3^-$
2: $R = -CH_2CONH_2$
3: $R = -CH_2CH_2CH_3$
4: $R = -CH(CH_3)_2$
5: $R = -CH_2CH_2CH_2OH$
6: $R = -CH_2CH_2OH$
7: $R = -CH_2CH_2COOH$
8: $R = -CH_2C_6H_5$
9: $R = -CH_3$
10: $R = -CH_2CH_3$
11: $R = -CH_2CH_2C_6H_5$ For MDEPT compound 1 is preferable. It is charged at physiological pH and is excluded from cells.

Compound 8 and compound 11 are not cosubstrates for NQO2 by our definition.

It is expected that charged or polar compounds (eg compounds 1, 7) will not readily enter cells. Lipophilic derivatives (eg compounds 3, 4) are expected to readily enter cells.

The invention will now be described in more detail by reference to the following Examples and Figures wherein FIG. 1 shows the bioactivation of CB 1954. The initial step is the reduction of CB 1954 by the enzyme DT diaphorase to form 5-(aziridin-1-yl)-4-hydroxylamino-2-nitrobenzamide. This hydroxylamine derivative can react with thioesters to produce DNA reactive species. It is postulated that this it the N-acetoxy derivative. The major product of this reaction is however 4-amino-5-(aziridin-1-yl)-2-nitrobenzamide that does not react readily with DNA. Formation of 4-amino-5-(aziridin-1-yl)-2-nitrobenzamide is in competition with the production of DNA binding products.

FIG. 6 shows the nucleotide sequence of a cDNA encoding human NQO2 and its deduced amino acid sequence (SEQ ID NO:2).

Figure 8A:
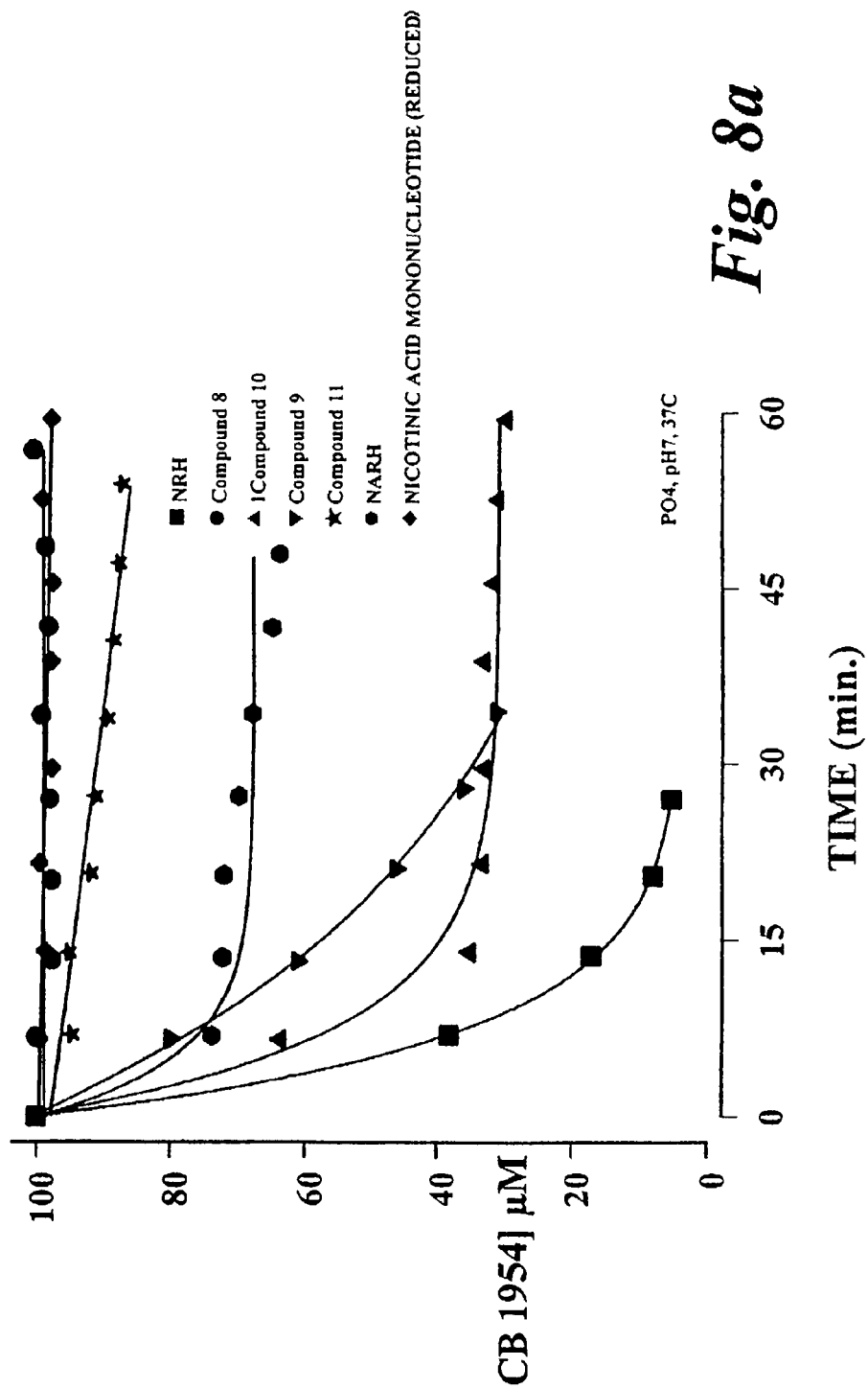

FIG. 8a shows the ability of NQO2 to use NRH and various analogues as co-substrates for the reduction of CB1954. In the absence of enzyme there was no CB1954 reduction (not shown). The initial concentration of co-substrate was 500 μm and the enzyme concentration was 1 μg/ml.

Figure 8B:
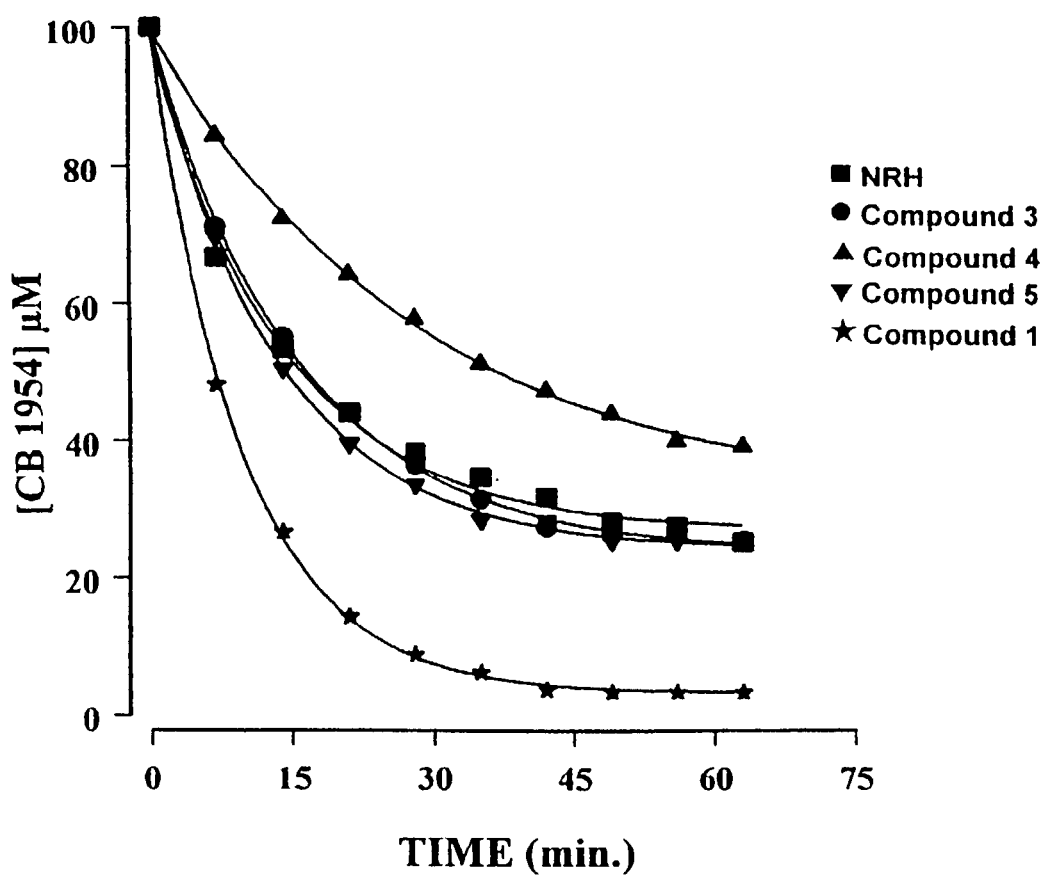

FIG. 8b shows the ability of NQO2 to use NRH and various analogues as co-substrates for the reduction of CB 1954. In the absence of enzyme there was no CB1954 reduction (not shown). The initial concentration of co-substrate was 500 μm and the enzyme concentration was 0.5 μg/ml.

Figure 8C:
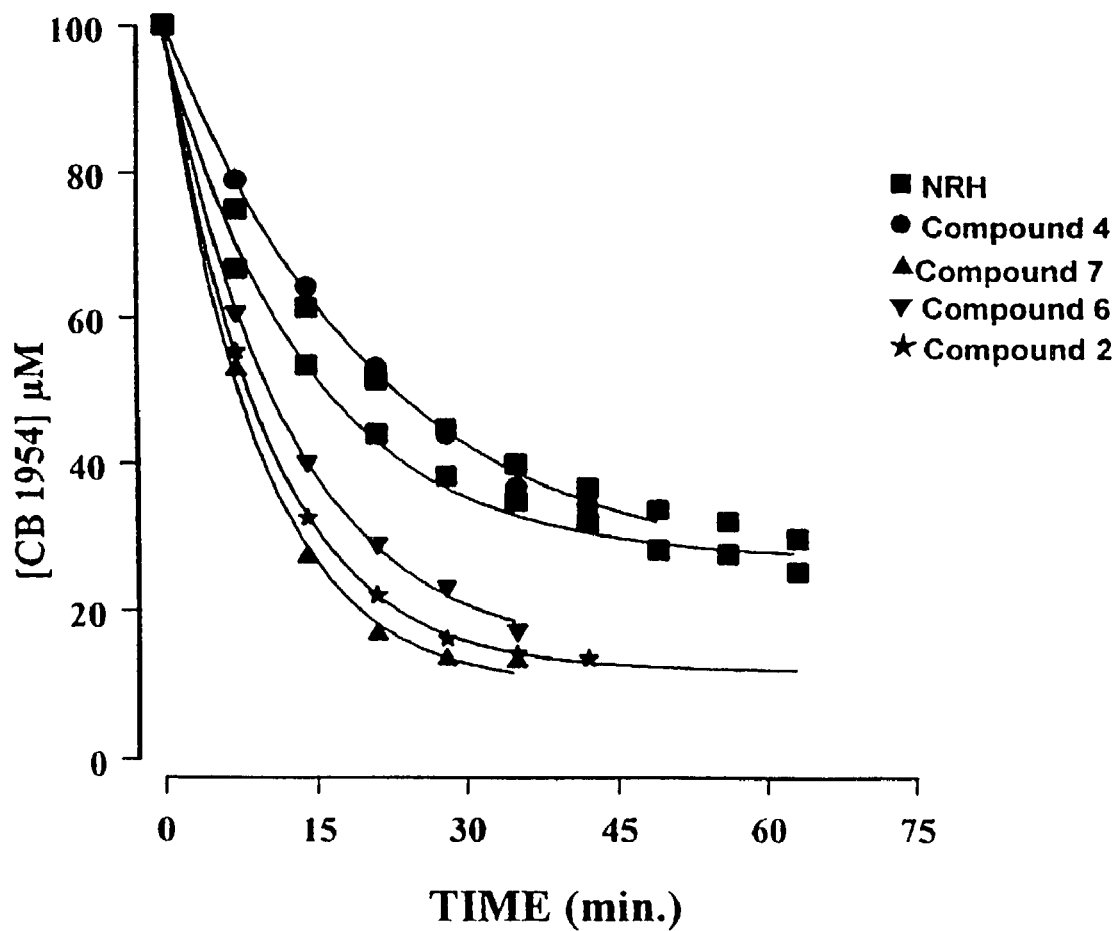

FIG. 8c shows the ability of NQO2 to use NRH and various analogues as co-substrates for the reduction of CB 1954. In the absence of enzyme there was no CB1954 reduction (not shown). The initial concentration of co-substrate was 500 μm and the enzyme concentration was 0.5 μg/ml.

Figure 9:
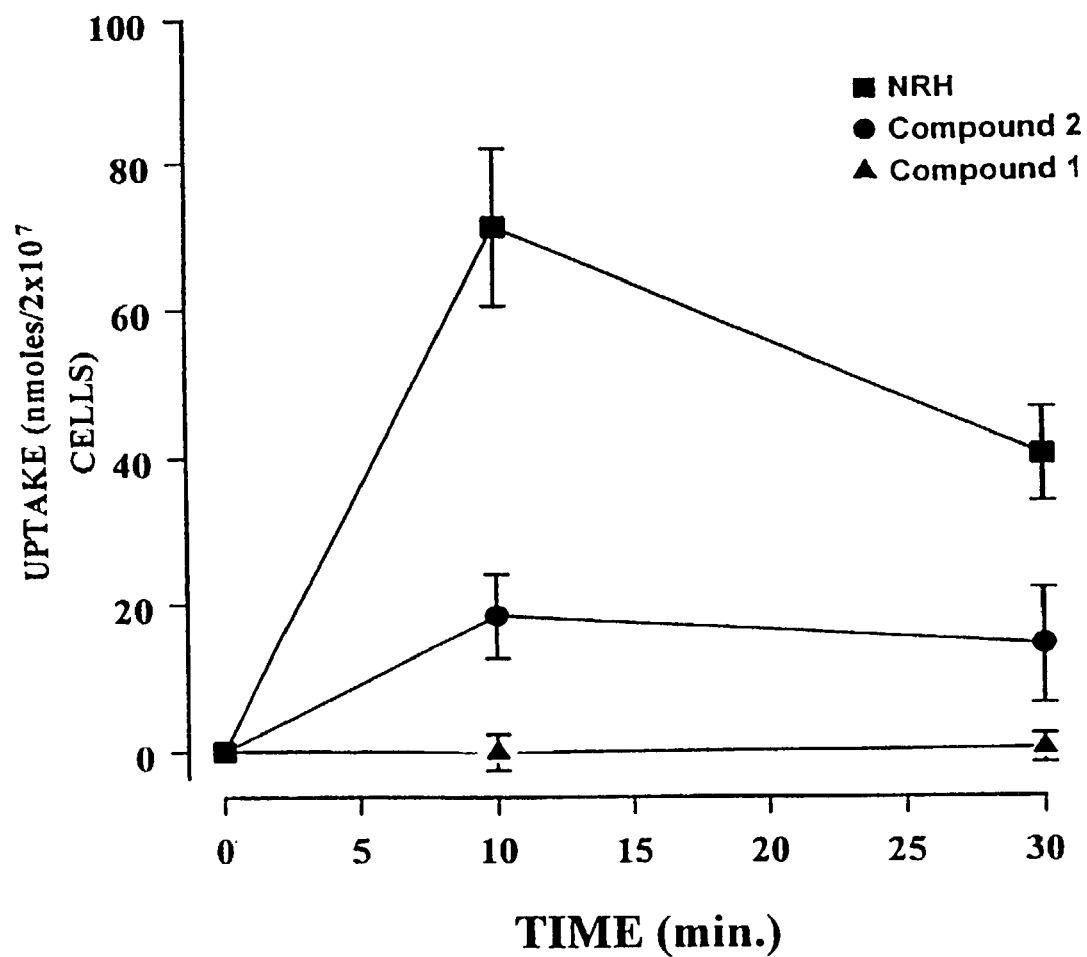

FIG. 9 shows the uptake of various co-substrates into wild-type V79 cells. Compound 1 is charged at physiological pH and is excluded from the cells. Thus this co-substrate is particularly suitable for MDEPT applications.

FIG. 10 shows the plasmids pIRES-P and H6.

Figure 11:
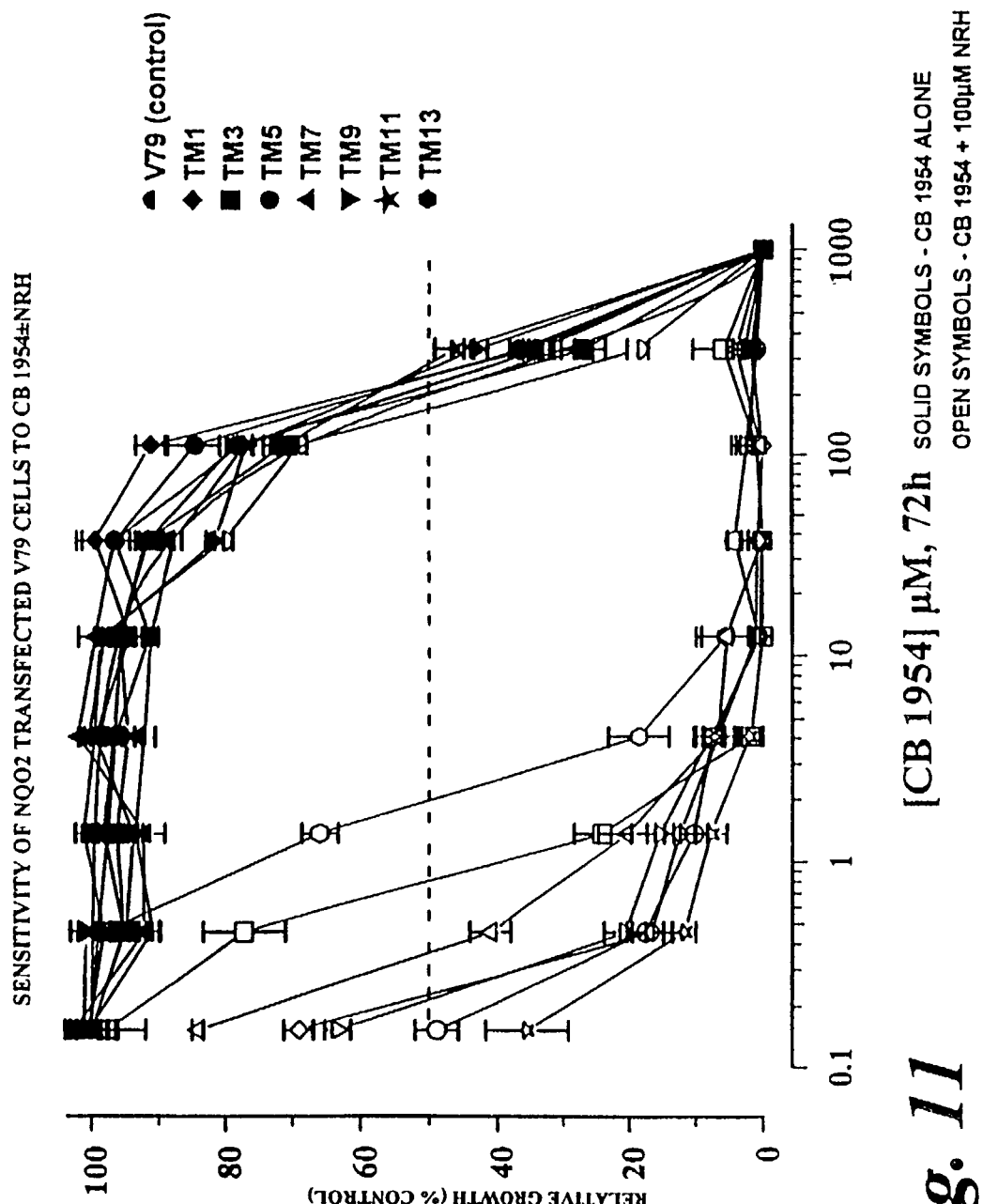

FIG. 11 shows the effect of NRH on the cytotoxicity of CB 1964 in NQO2 expressing V79 cells. The addition of NRH increased the cytotoxicity of CB 1954 by at least 100-fold (V79TM13) and was greater than 100-fold in the V79TM5 and 13 cell lines. This effect was not seen in non-transfected V79 cells (<3-fold) and can thus be ascribed to the expression of NQO2 in the transfected cells.

Figure 12:
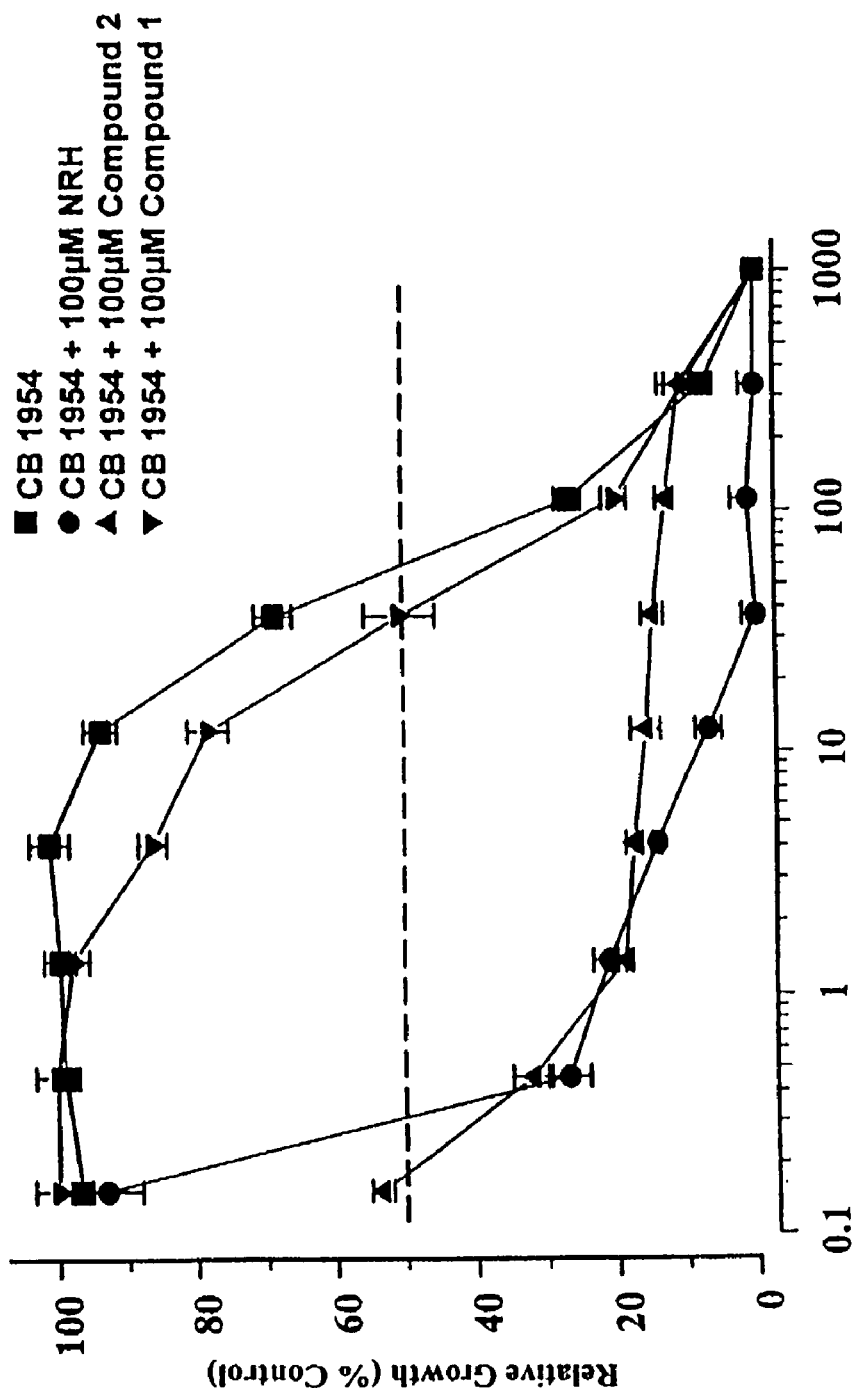

FIG. 12 shows the effect of NRH, compound 1 and compound 2 on the cytotoxicity of CB 1954 in human T98G gliobastoma cells. The cells were treated as for V79 cells but were treated for 144 hr in presence of CB 1954. The addition of NRH and compound 2 increased the cytotoxicity of CB 1954 by at least 100-fold whilst the impermeable co-substrate compound 1 did not potentiate.

Figure 13:
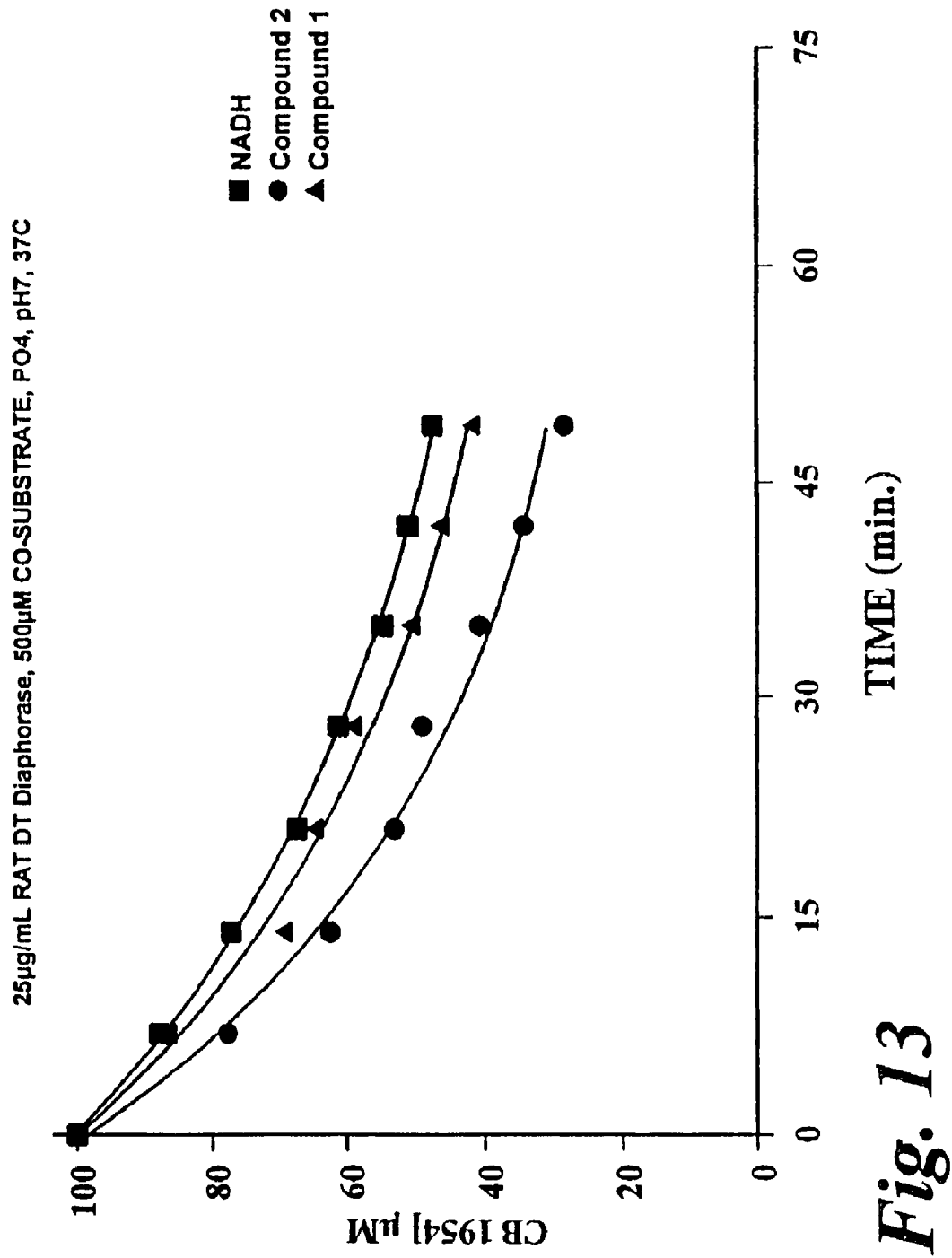

FIG. 13 shows the ability of rat DT diaphorase to utilise compounds 1 and 2 as co-substrates for the reduction of CB1954.

Figure 14:
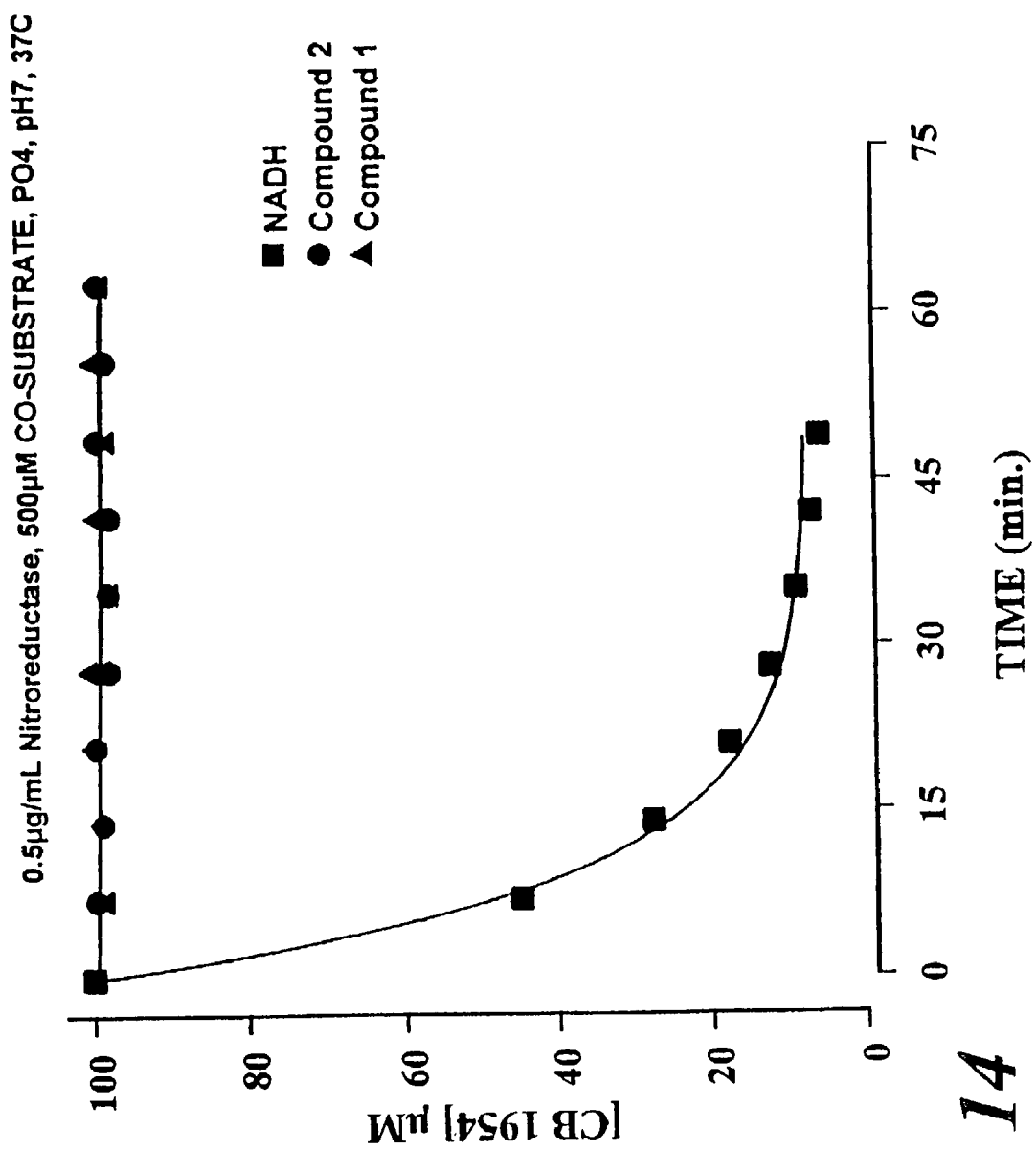

FIG. 14 shows the ability of E. coli nitroreductase to utilise compounds 1 and 2 as co-substrates for the reduction of CB1954.

Figure 15:
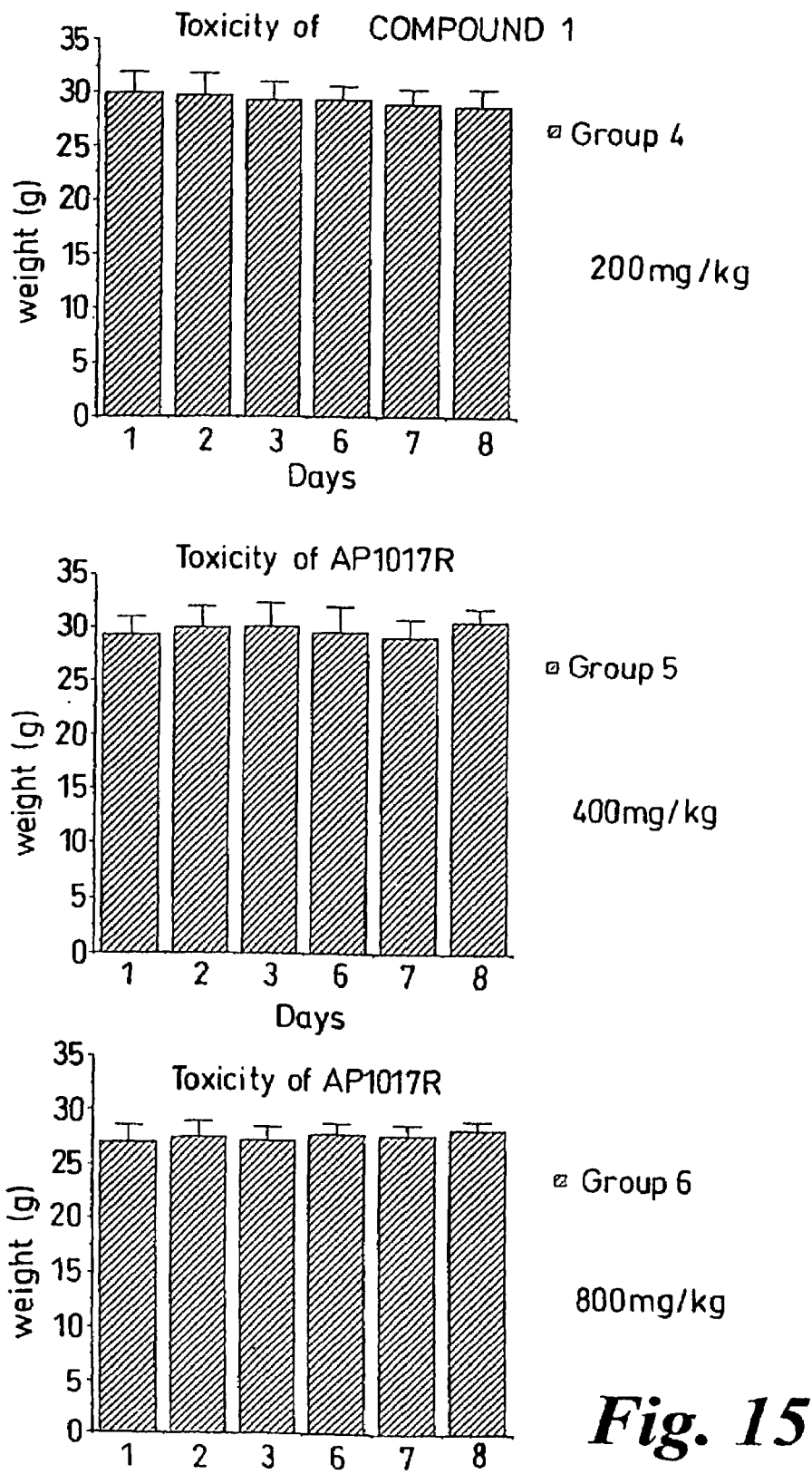

FIGS. 15 and 16 show the effect of compound 1 on the body weight of normal mice.

Figure 18:
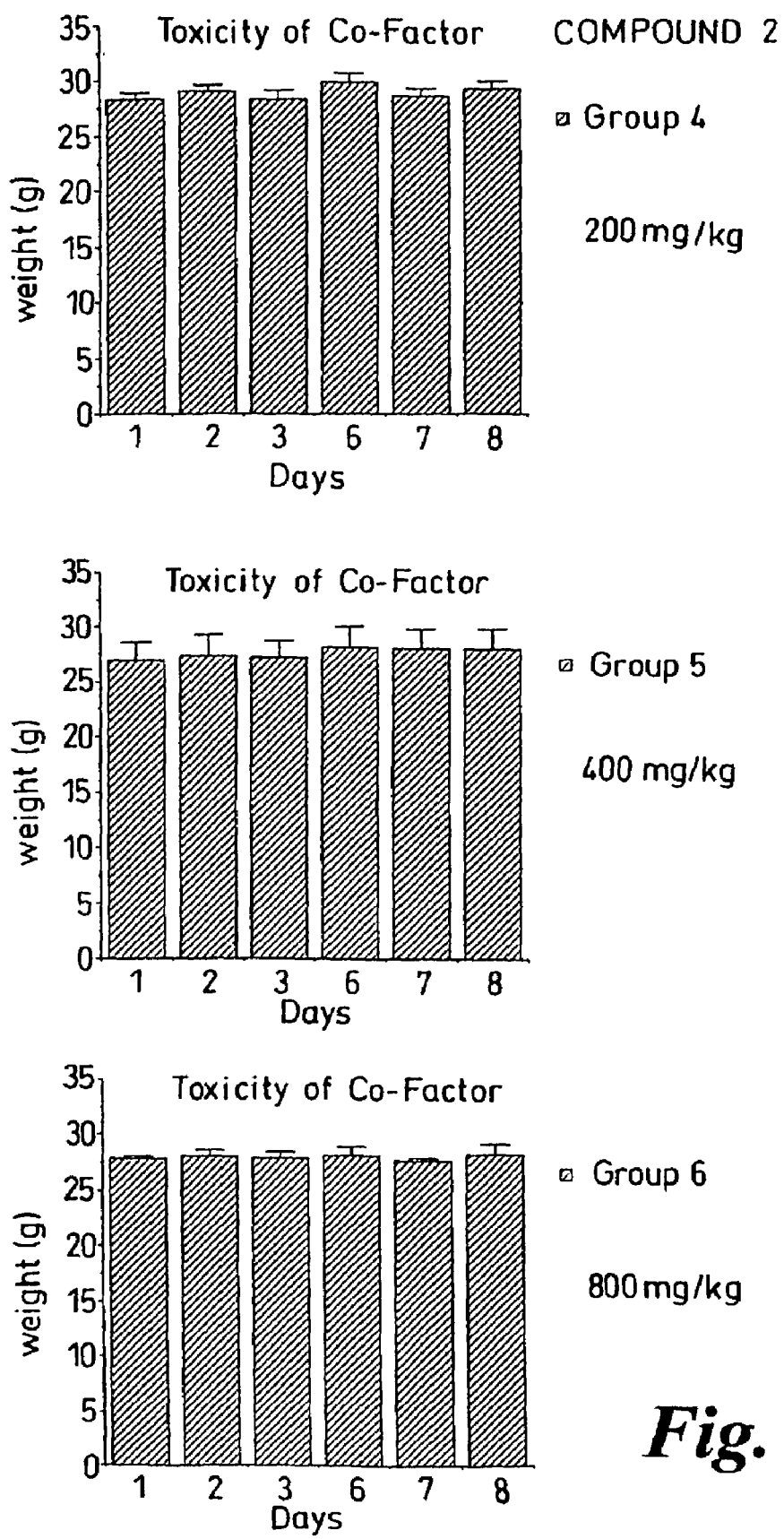

FIGS. 17 and 18 show the effect of compound 2 on the body weight of normal mice. Mice [6 groups of 3] were injected intravenously (tail vein) with either 1 or 2 at the doses shown and the weight of the mice was monitored over an 8 day period. Control mice received vehicle [phosphate buffered saline] only.

EXAMPLE 1

The effect of various co-substrates on human NQO2 activity

Experimental Details

Recombinant human NQO2 was prepared in E. coli. A NcoI and a HindIII restriction site were added to the 5' and 3'-ends of the full-length NQO2 cDNA, respectively, using a PCR method with primers and nucleotide sequences derived from the 5' and 3'-ends of the cDNA. The PCR product was resolved over a 1% agarose gel and then extracted using the QiAquick Gel Extraction Kit (Qiagen Inc). The gel-purified PCR product was cloned into PCRII vector from the TA cloning kit (Invitrogen Co) and the correct sequence of the PCR product was checked by dideoxy sequencing. The resulting construct was religated into the E. coli expression vector, pKK233-2 (Pharmacia) through the engineered NcoI and HindIII restriction sites. The expression plasmid was designated pKK-hNQO2. The pKK-hNQO2 E. coli cells were cultured, sonicated and centrifuged as previously described for the purification of recombinant DT diaphorase [Chen et al, 1992]. The supernatant from a 90 min-centrifugation at 105,00 g was applied to a 50 ml Affi-gel Blue (Bio-Rad) and the column was washed according to the published method. The purified NQO2 preparation was analysed by SDS-PAGE electrophoresis. The activity of NQO2 in the presence of CB 1954, and various cofactors was determined by HPLC. To determine the kinetic parameters NQO2 (1 μg/ml) was incubated with NRH (500 μM) and CB 1954 at different concentrations (0.1 to 2 mM) in sodium phosphate buffer (10 mM, pH7) at 37° C. At various times, aliquots (10 μl) were injected onto a Partisphere SCX (250×4.5 mm) HPLC column (Whatman Ltd) and eluted isocratically (1.5 ml/min) with 50 mM aqueous sodium phosphate containing 1% methanol. The eluate was continuously monitored for absorption at 320 nm. This separation system could resolve all the expected reduction products of CB1954 [Boland et al, 1991, Knox et al, 1992]. The reduction of CB 1954 was monitored by quantifying the increase in the area of the peak corresponding to the reduction product 5-(aziridin-1-yl)-4-hydroxylamino-2-nitrobenzamide. All the assays were initiated by addition of the enzyme and performed in duplicate. The kinetic parameters were calculated by plotting the initial rate of reduction at each concentration of CB 1954 against that concentration and fitting the data to the Michales-Menton equation using a computer programme (FigP). Values were confirmed by transforming the data and fitting it to various linear forms of the equation by regression analysis.

The effect of various co-substrates on CB 1954 was determined as above but NADH. NADPH or NMNH was substituted for the NRH and CB 1954 was used at a fixed concentration of 100 μM. The enzyme concentration was 5 μg/ml. The reduction of CB 1954 was monitored by measuring both the decrease in its corresponding peak area on the HPLC trace and the increase in the area of the peak corresponding to the reduction product 5-(aziridin-1-yl)-4-hydroxylamino-2-nitrobenzamide. The relative rates of reduction were determined at 10% reduction of CB1954 from a graph plotting CB 1954 reduction against time. The time axis was normalised to the equivalent of 10 μg/ml of NQO2.

TABLE 1

Kinetic parameters for NQO2, E. coli nitroreductase, human and rat DT-diaphorase with respect to CB 1954. NRH was used as a co-substrate for NQO2 whilst the values for the other enzymes were determined using NADH.

| ENZYME | Km (μM) | $k_{cat}$ ($s^{-1}$) |
|---|---|---|
| NQO2 | 263 ± 13 | 6.01 |
| Nitroreductase[1] | 862 ± 145 | 6.0 |
| Rat DT-diaphorase[2] | 826 | 0.0683 |
| Human DT-diaphorase[2] | 1403 | 0.0107 |

Data from:
[1][Anlezark et al, 1992]
[2][Boland et al, 1991]

TABLE 2

The relative rate of CB 1954 reduction by NQO2 using different co-substrates. All co-substrates were used at an initial concentration of 500 μM and CB 1954 was at an initial concentration of 100 μM.

| CO-SUBSTRATE | RELATIVE RATE OF REDUCTION |
|---|---|
| NADH | 1.0 |
| NADPH | 1.24 |
| NMNH | 5.6 |
| NRH | 70.0 |

EXAMPLE 2

Administration of a Monoclonal Antibody-NQO2 Conjugate

In this example the prodrug is administered 6–48 hours following administration of a monoclonal antibody-NQO2 conjugate. The exact interval depends upon the localisation characteristics of the conjugate but prodrug administration ideally commences as soon as the plasma activity of enzyme is insufficient to catalyse enough prodrug to cause toxicity. The dose of conjugate is in the range 100–300 mg m$^{-2}$ per patient. Administration of the cosubstrate NRH commences approximately 1 hour prior to the administration of prodrug and continues throughout the period of prodrug administration. The dose of prodrug depends upon its nature but an effective dose may be in the range 10–2000 mg m$^{-2}$. The dose of NRH may be 2–3 times the dose of prodrug. In this system it may be advantageous to accelerate clearance of residual enzyme activity from plasma and normal tissues. This may be achieved by administration of a galactosylated anti-enzyme antibody following conjugate administration but prior to administration of NRH.

EXAMPLE 3

Administration of a Recombinant NQO2 Polynucleotide

In this example a recombinant polynucleotide is administered. Administration may be by any route appropriate to the condition to be treated, suitable routes including oral, nasal and parenteral. The dosage is determined by the individual clinicians for individual patients and this is determined by the exact nature of the prodrug and the cytotoxic agent to be released from the prodrug. Approximate doses are given in Example 2 above. When the expression of NQO2 is at a useful level administration of NRH followed by prodrug can commence as detailed in Example 2.

EXAMPLE 4

Administration of NRH and prodrug

In this example a patient is administered NRH and after 1 hour concurrent administration of prodrug is started. As previously, the doses of prodrug and NRH will depend upon the nature of the prodrug and the cytotoxic agent released from the prodrug.

EXAMPLE 5

Potential Co-Substrates for NQO2

Figure 7:
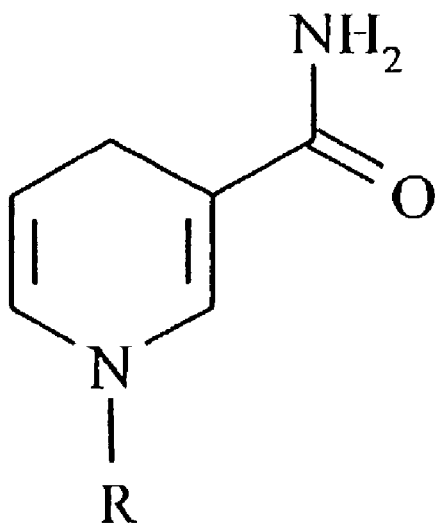
FIG. 7 shows the structures of potential co-substrates for NQO2.

The compounds synthesised are shown in FIG. 7. Details of the syntheses are now given.

Compound 1: 1-(3-sulfonatopropyl)-dihydronicotinamide

To a solution of 1-(3-sulfonatopropyl)-3-carboxamidopyridinium (20 mg) in water (5 mL) was added 50 mg of anhydrous sodium carbonate, 50 mg. of sodium bicarbonate and 50 mg of sodium hydrosulphite and the stoppered solution was allowed to stand at 37° for 30 min. The reduced compound was purified from the reaction mixture by preparative HPLC. 5 ml of reaction mixture was injected onto a Dynamax Macro C18 (21.4×250 mm) reverse-phase column (Rainin) and eluted by a gradient of acetonitrile in water (0–100% over 30 min) at 10.0 ml/min. The eluate was continually monitored at 340 nm and by fluorescence (ex 340, em 450) and a fraction corresponding to a peak of fluorescence collected. The eluate was collected and freeze-dried to provide compound 1. NMR ($D_2O$, 270 MHz, 20° C.) d 1.95–2.08 (m, J¯7.3 Hz, 2H, $NCH_2CH_2CH_2SO_3^-$), 2.94 (t, J=7.7 Hz, 2H, $NCH_2CH_2CH_2SO_3^-$), 3.04 (br t, J=1.8 Hz, 1H, 4-$CH_2$), 3.34 (t, J=6.8 Hz, 2H, $NCH_2CH_2CH_2SO_3^-$), 4.88–4.98 (m, 1H, H-5), 5.95 (dd, J=8.1 Hz, J=1.5 Hz, 1H, H-6), 7.04 (s, 1H, H-2).

The starting material 1-(3-sulfonatopropyl)-3-carboxamidopyridinium was prepared as follows:

1,3-Propanesultone (12.21 g, 0.10 mol) was added in one portion to a stirred solution of nicotinamide (12.21 g, 0.10 mol) in N,N-dimethylformamide (DMF,20 cm³). The clear solution was heated to 100° C. for 1 h, during which time (>5 min) a heavy colourless solid separated. The reaction mixture was cooled to room temperature, filtered, and the solid was washed serially with cold DMF (2×25 cm³) then dry diethyl ether (2×30 cm³). Recrystallisation from aqueous DMF gave 1-(3-sulfonalopropyl)-3-carboxamidopyridinium as colourless prisms: mp 300–302° C. dec; NMR ($D_2O$, 270 MHz, 20° C.) d 2.52 (quintet, J=7.3 Hz, 2H, $N^+CH_2CH_2CH_2SO_3^-$), 3.04 (t, J=7.3 Hz, 2H, $N^+CH_2CH_2CH_2SO_3^-$), 4.89 (t, J=7.3 Hz, 2H, $N^+CH_2CH_2CH_2SO_3^-$), 7.95 (br s, slow exchange, $CONH_2$), 8.24 (br t, J¯7.2 Hz, 1H, H-5), 8.94 (d, J=8.1 Hz, 1H, H-4), 9.10 (d, J=6.2 Hz, 1H, H-6), 9.40 (s, 1H, H-2). Found: C, 43.38; H, 4.95; N, 10.94%. $C_9H_{12}N_2O_4S \cdot 0.25H_2O$(anhydrous M=244.27) requires C, 43.45; H, 5.06; N, 11.26%.

Compound 2

Compound 2, 1-(carboxamidomethyl)-dihydronicotinamide, was prepared from 1-(carboxamidomethyl)-3-carboxamidopyridinium iodide following the reduction procedure described for compound 1.

NMR ($D_2O$, 270 MHz, 20° C.) d 3.00 (br t, J=1.8 Hz, 2H, 4-$CH_2$), 3.90 (s, 2H, $CH_2CONH_2$), 4.82–4.90 (m, 1H, H-5), 5.76 (dm, J=8.1 Hz, H-6), 6.89 (s, 1H, H-2).

The starting material 1-(carboxamidomethyl)-3-carboxamidopyridinium iodide was prepared by heating a mixture of nicotinamide (2.0 g, 16.4 mmol) and 2-iodoacetamide (3.1 g, 16.8 mmol) in DMF (5 ml) at 55–60° C. for 3 h. After cooling to room temperature ethyl acetate (50 ml) was added and the mixture was stirred for 30 min. The product was removed by filtration, dried at the pump and recrystallised from aqueous ethanol to give 1-(carboxamidomethyl)-3-carboxamidopyridinium iodide as colourless crystals (3.3 g, 66%): mp 210–211° C. Found: C, 31.37; H, 3.34; N, 13.77%. $C_8H_{10}N_3O_2I$ (anhydrous M=307.09) requires C, 31.29; H, 3.28; N, 13.68%.

Compound 3

Compound 3, 1-propyl-dihydronicotinamide, was prepared from 1-propyl-3-carboxamidopyridinium bromide following the reduction procedure described for compound 1. NMR ($CDCl_3$, 270 MHz, 20° C.) d 0.90 (t, J=7.3 Hz, 3H, $NCH_2CH_2CH_3$), 1.56 (sextet, J=7.3 Hz, 2H, $NCH_2CH_2CH_3$), 3.05 (t, J=7.3 Hz, 2H, $NCH_2CH_2CH_3$), 3.16 (dd, J=3.6 Hz, J=1.8 Hz, 2H, 4-$CH_2$), 4.72 (dt, J=8.1 Hz, J=3.6 Hz, 1H, H-5), 5.35 (br s, 2H, slow $D_2O$ exchange, $CONH_2$), 5.72 (dq, J=8.1 Hz, 1.8 Hz, 1H, H-6), 7.04 (d, J=1.8 Hz, H-2).

The starting material 1-propyl-3-carboxamidopyridinium bromide was prepared as follows. A solution of nicotinamide (12.21 g, 0.10 mol) and 1-bromopropane (12.30 g, 0.10 mol) in DMF (20 cm³) was stirred and heated to 70° C. for 1 h. A heavy precipitate appeared within 15 min. After cooling to room temperature overnight, the mixture was filtered and the solid washed with cold DMF (10 cm³) then dry diethyl ether (2×20 cm³). Recrystallisation from DMF gave 1-propyl-3-carboxamidopyridinium bromide (19.42 g, 79%) as colourless prisms:

mp 171.5–172.5° C.; NMR ($d_6$-DMSO, 270 MHz, 20° C.) d 0.91 (t, J=7.3 Hz, 3H, $N^+CH_2CH_2CH_3$), 2.01 (sextet, J=7.3 Hz, 2H, $N^+CH_2CH_2CH_3$), 4.70 (t, J=7.3 Hz, 2H, $N^+CH_2CH_2CH_3$), 8.20 (br s, slow $D_2O$ exchange, 1H, $CONH_aH_b$), 8.32 (dd, J=8.1 Hz, J=6.2 Hz, 1H, H-5), 8.68 (br s, slow $D_2O$ exchange, 1H, $CONH_aH_b$), 9.02 (d, J=8.1 Hz, 1H, H-4), 9.35 (d, J=6.2 Hz, 1H, H-6), 9.65 (s, 1H, H-2). Found: C, 44.21; H, 5.36; N, 11.32%. $C_9H_{13}N_2OBr$ (anhydrous M=245.12) requires C, 44.10; H, 5.35; N, 11.43%.

Compound 3 could also be prepared by reduction of 1-propyl-3-carboxamidopyridinium iodide. This starting material was prepared by heating a mixture of nicotinamide (2.0 g, 16.4 mmol) and 1-iodopropane (3.2 ml, 32.8 mmol) in DMF (5 ml) at 90–95° C. for 4 h. Ethyl acetate (50 ml) was added to the cooled solution and the mixture was stirred at room temperature for 30 min. The solid was filtered, dried at the pump and recrystallised from methanol to give 1-propyl-3-carboxamidopyridinium iodide as pale yellow crystals (2.3 g, 48%): mp 183–184° C. (lit. 180–182° C. [S. Liao, J. T. Dulaney & H. G. Williams-Ashman, *J Biol Chem.*, 237, 2981–2987 (1962)]; NMR ($d_6$-DMSO, 270 MHz, 20° C.) δ 0.90 (t, 3H), 1.98 (m, 2H), 4.64 (t, 2H), 8.17 (s, 1H), 8.30 (t, 1H), 8.54 (s, 1H), 8.94 (d, 1H), 9.23 (s, 1H), 9.49 (s, 1H). Found: C, 37.05; H, 4.47; N, 9.49%. $C_9H_{13}N_2OI$ (anhydrous M=292.12) requires C, 37.01; H, 4.49; N, 9.59%.

Compound 4

Compound 4, 1-(2-propyl)-dihydronicotinamide, was prepared from 1-(2-propyl)-3-carboxamidopyridinium bromide following the reduction procedure described for compound 1.

The starting material 1-(2-propyl)-3-carboxamidopyridinium bromide was prepared as follows. A solution of nicotinamide (12.21 g, 0.10 mol) and 2-bromopropane (12.30 g, 0.10 mol) in DMF (20 cm³) was stirred and heated to 70° C. for 10 h, during which time a colourless precipitate appeared. After cooling to room temperature overnight, the mixture was filtered and the solid washed with cold DMF (10 cm³) then dry diethyl ether (2×20 cm³). Recrystallisation from DMF gave 1-(2-propyl)-3-carboxamidopyridinium bromide (16.81 g, 69%) as colourless prisms: mp 215.5–217.0° C.; NMR ($d_6$-DMSO, 270 MHz, 20° C.) d 1.68 (d, J=7.0 Hz, 6H, $N^+CH(CH_3)_2$), 5.17 (septet, J=7.0 Hz, 2H, $N^+CH(CH_3)_2$), 8.20 (br s, slow $D_2O$ exchange, 1H, $CONH_aH_b$), 8.31 (dd, J=8.1 Hz, J=6.2 Hz, 1H, H-5), 8.71 (br s, slow $D_2O$ exchange, 1H, $CONH_aH_b$), 8.98 (d, J=8.1

Hz, 1H, H-4), 9.43 (d, J=6.2 Hz, 1H, H-6), 9.62 (s, 1H, H-2). Found: C, 44.19; H. 5.34; N, 11.30%. $C_9H_{13}N_2OBr$ (anhydrous M=245.12) requires C, 44.10; H, 5.35; N, 11.43%.

Compound 4 could also be prepared by reduction of 1-(2-propyl)-3-carboxamidopyridinium iodide. This was prepared by heating a mixture of nicotinamide (2.0 g, 16.4 mmol) and 2-iodopropane (3.0 ml, 30.0 mmol) in DMF (5.0 ml) at 90–95° C. for 4 h. Ethyl acetate (50 ml) was added to the cooled solution and the mixture was stirred at room temperature for 30 min. The mixture was filtered and the solid was dried at the pump and recrystallised from aqueous ethanol to give 1-(2-propyl)-3-carboxamidopyridinium iodide as yellow crystals (1.1 g, 23%): mp 188–189° C. Found: C, 37.16; H, 4.55; N, 9.53%. $C_9H_{13}N_2OI$ (anhydrous M=292.12) requires C, 37.01; H, 4.49; N, 9.59%.

Compound 5

Compound 5, 1-(3-hydroxypropyl)-dihydronicotinamide, was prepared from 1-(3-hydroxypropyl)-3-carboxamidopyridinium bromide following the reduction procedure described for compound 1.

NMR ($D_2O$, 270 MHz, 20° C.) d 1.89 (br quintet, J⁻6.6 Hz, 2H, $NCH_2CH_2CH_2OH$), 3.17 (br t, J=1.8 Hz, 2H, 4-$CH_2$), 3.38 (t, J=6.9 Hz, 2H, $NCH_2CH_2CH_2OH$), 3.74 (t, J=6.2 Hz, 2H, $NCH_2CH_2CH_2OH$), 4.95–5.05 (m, 1H, H-5), 6.01 (dm, J=8.1 Hz, 1H, H-6), 7.13 (s, 1H, H-2).

The starting material 1-(3-hydroxypropyl)-3-carboxamidopyridinium bromide was prepared as follows. A solution of nicotinamide (12.21 g, 0.10 mol) and 3-bromo-1-propanol (13.90 g, 0.10 mol) in DMF (20 cm³) was stirred and heated to 90° C. for 1 h. After cooling to room temperature overnight, the mixture was filtered and the solid washed with cold DMF (10 cm³) then dry diethyl ether (2×25 cm³). Recrystallisation from DMF gave 1-(3-hydroxypropyl)-3-carboxamidopyridinium bromide (19.29 g, 74%) as colourless prisms: mp 119.0–120.0° C.; NMR ($d_6$-DMSO, 270 MHz, 20° C.) d 2.14 (br quintet, J⁻6.2 Hz, 2H, $N^+CH_2CH_2CH_2OH$), 3.48 (t, J=5.7 Hz, 2H, $N^+CH_2CH_2CH_2OH$), 4.77 (t, J=7.0 Hz, 2H, $N^+CH_2CH_2CH_2OH$), 8.18 (br s, slow $D_2O$ exchange, 1H, $CONH_aH_b$), 8.28 (dd, J=8.1 Hz, J=5.9 Hz, 1H, H-5), 8.63 (br s, slow $D_2O$ exchange, 1H, $CONH_aH_b$), 8.97 (d, J=8.1 Hz, 1H, H-4), 9.26 (d, J=5.9 Hz, 1H, H-6), 9.56 (s, 1H, H-2). Found: C, 40.07; H, 5.17; N, 10.16%. $C_9H_{13}N_2O_2Br.0.5H_2O$ (anhydrous M=261.12) requires C, 40.02; H, 5.22; N, 10.37%.

Compound 6

Compound 6, 1-(2-hydroxyethyl)-dihydronicotinamide, was prepared from 1-(2-hydroxyethyl)-3-carboxamidopyridinium iodide following the reduction procedure described for compound 1.

The starting material 1-(2-hydroxyethyl)-3-carboxamidopyridinium iodide was prepared by heating a mixture of nicotinamide (2.0 g, 16.4 mmol) and 2-iodoethanol (2.6 ml, 33.3 mmol) in DMF (5 ml) at 90–95° C. for 4 h. Ethyl acetate (50 ml) was added to the cooled solution and the mixture was stirred at room temperature for 30 min. The mixture was filtered and the solid was dried at the pump and recrystallised from methanol to give 1-(2-hydroxyethyl)-3-carboxamidopyridinium iodide as colourless crystals (3.8 g, 79%): mp 128–129° C. NMR ($d_6$-DMSO, 270 MHz, 20° C.) d 3.90 (br t, J=7.3 Hz, 2H, $N^+CH_2CH_2OH$), 5.21 (t, J=7.3 Hz, 2H, $N^+CH_2CH_2OH$), 8.17 (br s, slow $D_2O$ exchange, 1H, $CONH_aH_b$), 8.32 (dd, J=8.1 Hz, J=6.2 Hz, 1H, H-5), 8.56 (br s, slow $D_2O$ exchange, 1H, $CONH_aH_b$), 8.98 (d, J=8.1 Hz, 1H, H-4), 9.16 (d, J=6.2 Hz, 1H, H-6), 9.43 (s, 1H, H-2). Found: C, 33.06; H, 3.85; N, 9.57%. $C_8H_{11}N_2O_2I$ (anhydrous M=294.09) requires C, 32.67; H, 3.77; N, 9.53%.

Compound 7

Compound 7, 1-(2-carboxyethyl)-dihydronicotinamide, was prepared from 1-(2-carboxyethyl)-3-carboxamidopyridinium iodide according to the reduction procedure described for compound 1.

NMR ($D_2O$, 270 MHz, 20° C.) 2.46 (t, J=6.9 Hz, 2H, $NCH_2CH_2CO_2H$), 2.96 (t, J=6.9 Hz, 2H, $NCH_2CH_2CO_2H$), 4.85–4.95 (m, 1H, H-5), 7.33–7.31 (m,), 8.19–8.24 (m), 8.29–9.05 (m), 9.36 (s).

The starting material 1-(2-carboxyethyl)-3-carboxamidopyridinium iodide was prepared by heating a mixture of nicotinamide (2.0 g, 16.4 mmol) and 3-iodopropionic acid (3.3 g, 16.5 mmol) in DMF (5 ml) at 90–95° C. for 4 h. Ethyl acetate (50 ml) was added to the cooled solution and the mixture was stirred at room temperature for 30 min. The mixture was filtered and the solid was dried at the pump and recrystallised from aqueous ethanol to give 1-(2-carboxyethyl)-3-carboxamidopyridinium iodide as colourless crystals (2.4 g, 46%): mp 185–186° C. Found: C, 33.80; H, 3.45; N, 8.57%. $C_9H_{11}N_2O_3I$ (anhydrous M=322.10) requires C, 33.56; H, 3.44; N, 8.70%.

Compound 8

Compound 8 1-benzyl-dihydronicotinamide was prepared from 1-benzyl-3-carboxamidopyridinium iodide according to the reduction procedure described for compound 1.

1-benzyl-3-carboxamidopyridinium bromide was prepared by heating a mixture of nicotinamide (2.0 g, 16.4 mmol) and benzyl bromide (3.9 ml, 32.8 mmol) in DMF (5 ml) at 55–60° C. After ⁻5 minutes a heavy precipitate formed and a further portion of DMF (5 ml) was added. After 30 min the mixture was cooled to room temperature and ethyl acetate (50 ml) was added. The mixture was stirred at room temperature for 30 min then the solid was filtered, dried at the pump and recrystallised from aqueous ethanol to give 1-benzyl-3-carboxamidopyridinium bromide as colourless prisms (4.2 g, 85%): mp 212–213° C. NMR ($d_6$-DMSO, 270 MHz, 20° C.) d 5.99 (s, 2H, $N^+CH_2Ph$), 7.35–7.55 (m, 3H, H-3'/4'/5'), 7.55–7.70 (m, 2H, H-2'/6'), 8.22 (br s, slow $D_2O$ exchange, 1H, $CONH_aH_b$), 8.32 (dd, J=8.1 Hz, J=6.2 Hz, 1H, H-5), 8.68 (br s, slow $D_2O$ exchange, 1H, $CONH_aH_b$), 9.03 (d, J=8.1 Hz, 1H, H-4), 9.39 (d, J=6.2 Hz, 1H, H-6), 9.74 (s, 1H, H-2). Found: C, 53.35; H, 4.48; N, 9.40%. $C_{13}H_{13}N_2OBr$ (anhydrous M=293.16) requires C, 53.26; H, 4.47; N, 9.56%.

Compound 9

Compound 9: 1-methyl-dihydronicotinamide was prepared from 1-methyl-3-carboxamidopyridinium iodide according to the reduction procedure described for compound 1.

The starting material 1-methyl-3-carboxamidopyridinium iodide, was obtained from Sigma-Aldrich Chemical Company, Poole Dorset, UK.

NMR ($d_6$-DMSO, 270 MHz, 20° C.) d 4.41 (s, 3H, $N^+CH_3$), 8.16 (br s, slow $D_2O$ exchange, 1H, $CONH_aH_b$), 8.26 (dd, J=8.4 Hz, J=6.2 Hz, 1H, H-5), 8.52 (br s, slow $D_2O$ exchange, 1H, $CONH_aH_b$), 8.91 (d, J=8.4 Hz, 1H, H-4), 9.12 (d, J=6.2 Hz, 1H, H-6), 9.41 (s, 1H, H-2).

Compound 10

Compound 10, 1-ethyl-dihydronicotinamide, was prepared from 1-ethyl-3-carboxamidopyridinium iodide according to the reduction procedure described for compound 1.

The starting material 1-ethyl-3-carboxamidopyridinium iodide was prepared by heating a mixture of nicotinamide (2.0 g, 16.4 mmol) and 1-iodoethane (2.6 ml, 32.5 mmol) in DMF (5 ml) at 55–60° C. for 3 h. After cooling, ethyl acetate (50 ml) was added and the mixture was stirred at room temperature for 30 min. The mixture was filtered and the pale yellow solid was dried at the pump and recrystallised from a mixture of DMF and ethyl acetate to give 1-ethyl-3-carboxamidopyridinium iodide as pale yellow prisms (3.7 g, 82%): mp 202–203° C. NMR ($d_6$-DMSO, 270 MHz, 20° C.) d 1.59 (t, J=7.3 Hz, 3H, $N^+CH_2CH_3$), 4.72 (q, J=7.3 Hz, 2H, $N^+CH_2CH_3$), 8.16 (br s, slow $D_2O$ exchange, 1H, $CONH_aH_b$), 8.30 (dd, J=8.1 Hz, J=6.2 Hz, 1H, H-5), 8.53 (br s, slow $D_2O$ exchange, 1H, $CONH_aH_b$), 8.93 (d, J=8.1 Hz, 1H, H-4), 9.27 (d, J=6.2 Hz, 1H, H-6), 9.50 (s, 1H, H-2). Found: C, 34.11; H, 3.91; N, 9.80%. $C_8H_{11}N_2OI$ (anhydrous M=278.09) requires C, 34.55; H, 3.99; N, 10.07%.

Compound 11

Compound 11, 1-phenylethyl-dihydronicotinamide, was prepared from 1-phenylethyl-3-carboxamidopyridinium iodide according to the reduction procedure described for compound 1.

The starting material 1-phenylethyl-3-carboxamidopyridinium iodide was prepared by heating a mixture of nicotinamide (2.0 g, 16.4 mmol) and (2-iodoethyl) benzene (4.7 ml, 32.5 mmol) in DMF (5 ml) at 55–60° C. for 4 h. Ethyl acetate (50 ml) was added to the cooled solution and the mixture was stirred at room temperature for 30 min. The solid was filtered, dried at the pump and recrystallised from aqueous ethanol to give 1-phenylethyl-3-carboxamidopyridinium iodide as yellow prisms (3.8 g, 65%): mp 188–189° C. NMR (d6-DMSO, 270 MHz, 20° C.) d 3.32 (t., J=7.3 Hz, 2H, $N^+CH_2CH_2Ph$), 4.93 (t., J=7.3 Hz, 2H, $N^+CH_2CH_2Ph$), 7.15–7.40 (m, 5H, H-2'/3'/4'/5'/6'), 7.55–7.70 (m, 2H, H-2'/6') 8.17 (br s, slow $D_2O$ exchange, 1H, $CONH_aH_b$), 8.26 (dd, J=8.1 Hz, J=6.2 Hz, 1H, H-5), 8.52 (br s, slow $D_2O$ exchange, 1H, $CONH_aH_b$), 8.93 (d, J=8.1 Hz, 1H, H-4), 9.15 (d, J=6.2 Hz, 1H, H-6), 9.47 (s, 1H, H-2).

We have examined compounds 1–11 as potential co-substrates for NQO2 and we have determined full kinetic properties for compounds 1 and 2. Experimental details and results are given below.

Compounds 3, 8, 9 and 10 have been reported in the literature (S Liao, J T Dulaney & H G Williams-Ashman, *J. Biol. Chem.*, 237, 2981–2987, 1962; S Liao & H G Williams-Ashman, *Biochem. and Biophys. Res. Comm.*, 4, 208–213, 1961; S Liao & H G Williams-Ashman, *Biochem. Pharmacol.*, 6, 53–54, 1961.)

Figure 1:
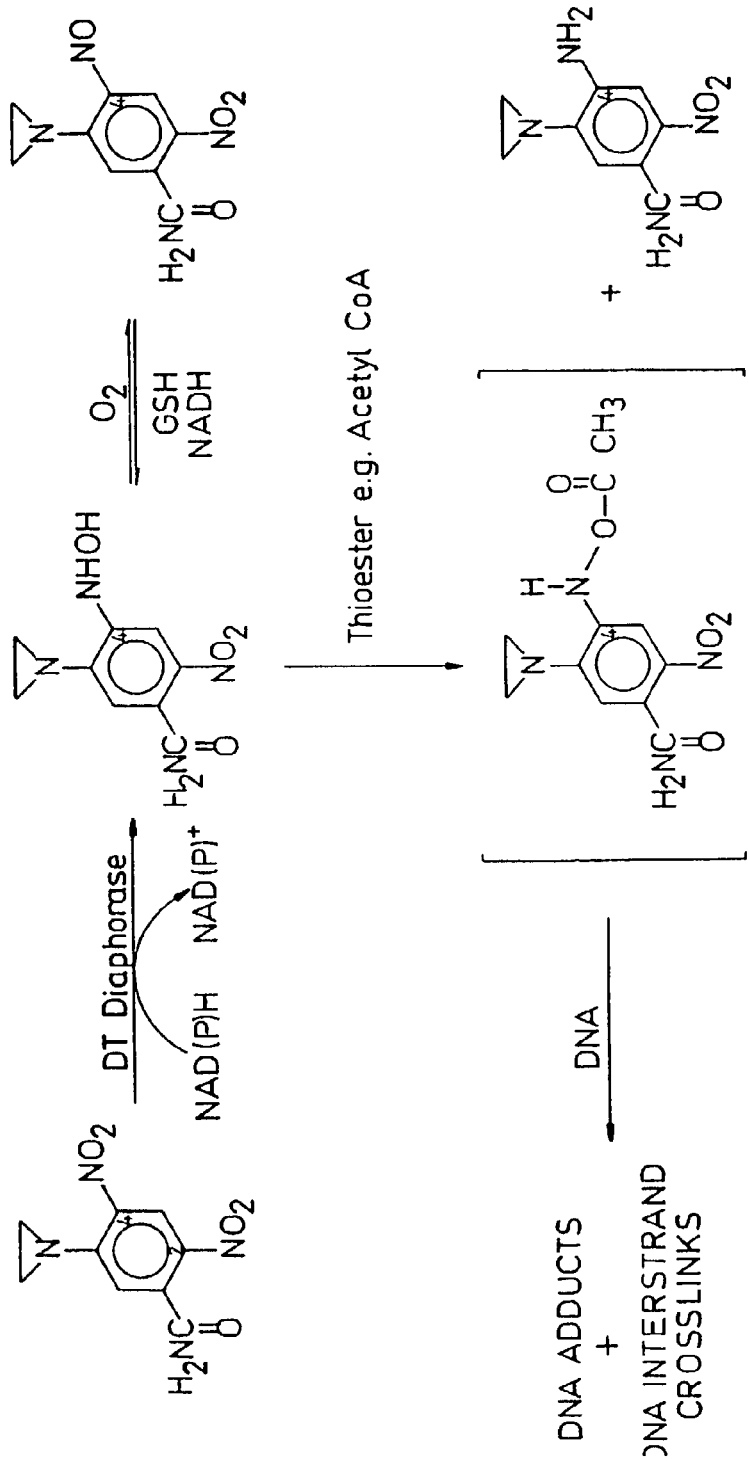
Figure 2:
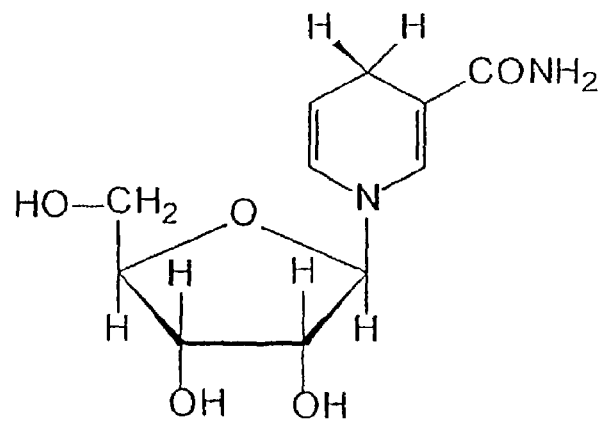
FIG. 2 shows the structure of NRH.
Figure 3:
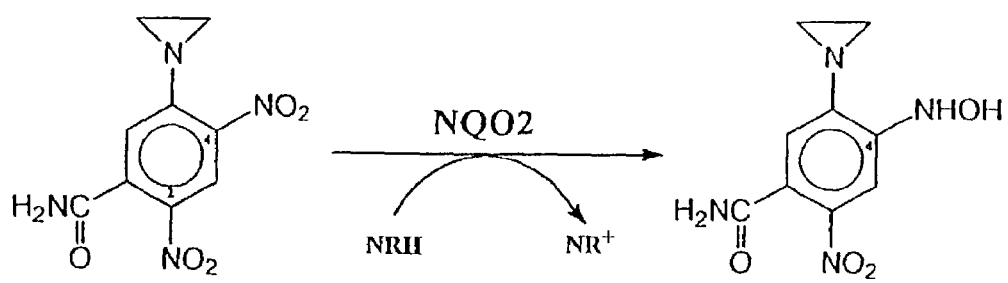
FIG. 3 is a schematic representation of the bioactivation of CB 1954 by NQO2.
Figure 4:
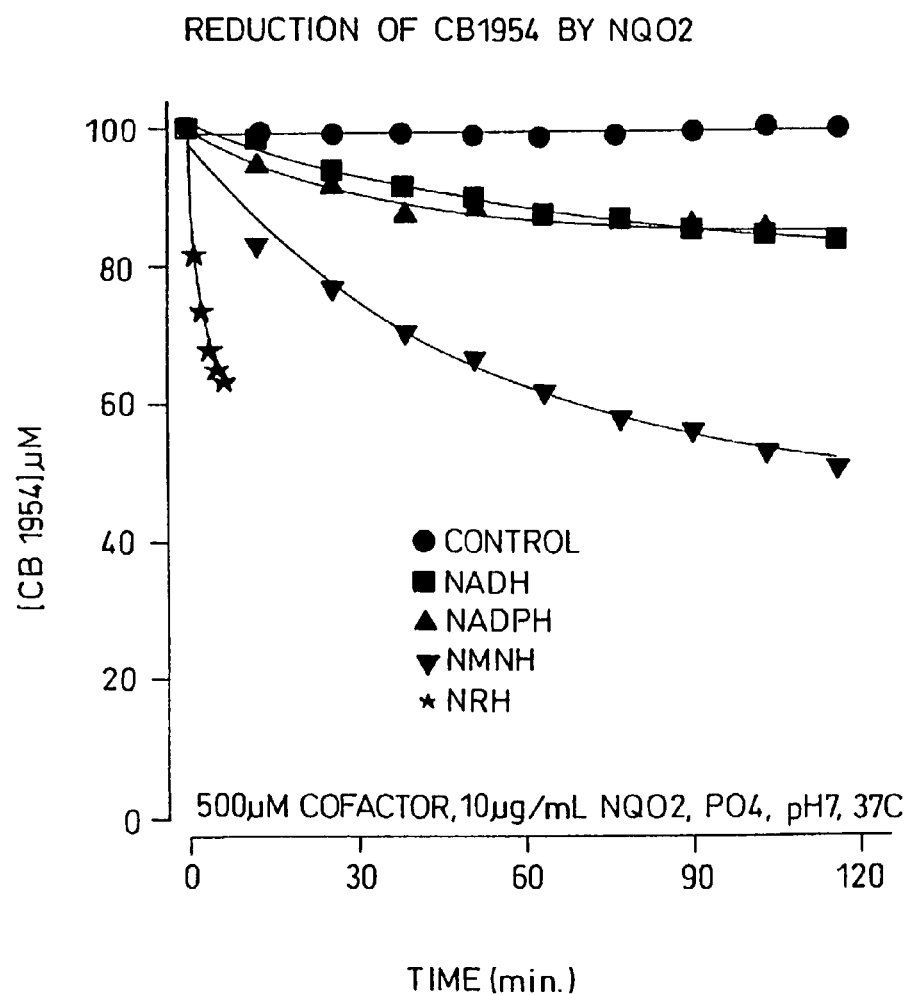
FIG. 4 shows the reduction of CB 1954 by NQO2 in the presence of various cosubstrates.
Figure 5:
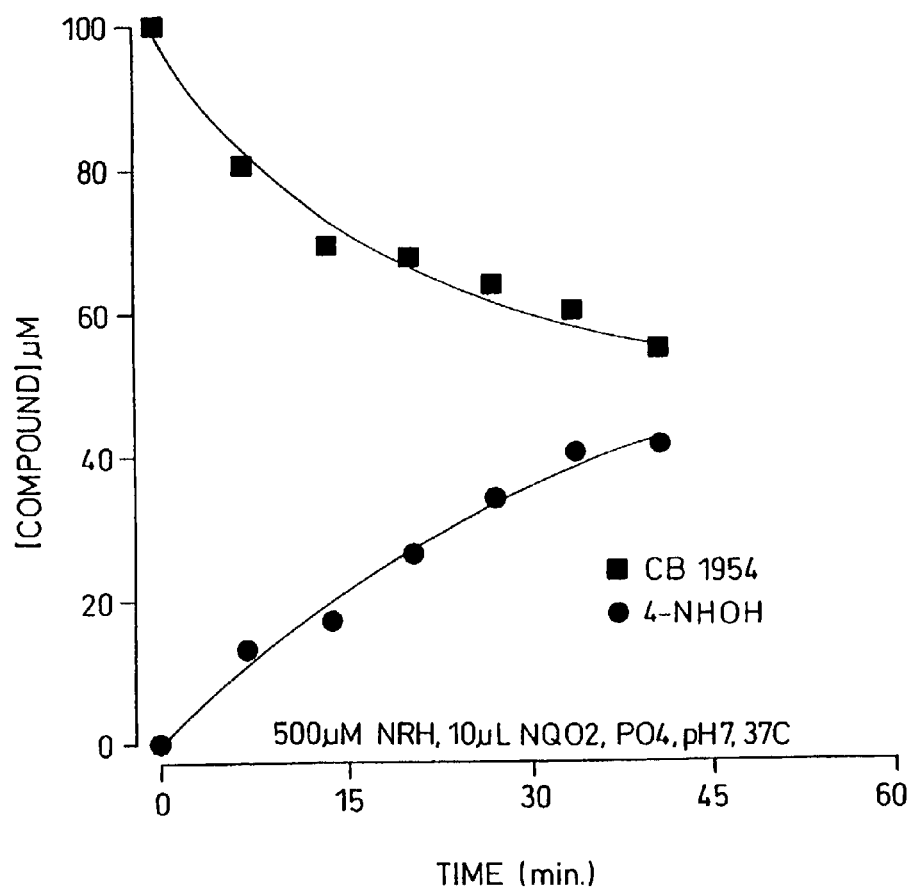
FIG. 5 shows the formation of 5-(aziridin-1-yl)-4-hydroxylamino-2-nitrobenzamide (4-NHOH) from the reduction of CB 1954 by NQO2.

FIG. 8a shows that compound 8 and nicotinic acid mononucleotide (reduced) are not co-substrates for NQO2 and that compound 11 is a poor co-substrate. FIG. 4 shows that NADH and NADPH are poor co-substrates for NQO2.

The $k_{cat}$ of NQO2 with NRH is 360 min$^{-1}$ using CB 1954 as an electron acceptor. The $K_m$ for this reaction is about 30 μM. The new cofactors are certainly very good at reducing CB 1954 in the presence of NQO2.

Determination of Co-Substrate Activity with NQO2

The activity of various potential co-substrates was determined by HPLC analysis in the presence of CB1954 and NQO2. To determine the kinetic parameters NQO2 (1 μg/ml) was incubated with NRH (5000 μM) and CB1954 at different concentrations (0.1 to 2 mM) in sodium phosphate buffer (10MM, pH 7) at 37° C. At various times, aliquots (10 μl) were injected onto a Partisphere SCX (250×4.5 mm) HPLC column (Whatman Ltd) and eluted isocratically (1.5 ml/min) with 50 mM aqueous sodium phosphate containing 1% methanol. The eluate was continuously monitored for absorption at 320 nm. This separation system could resolve all the expected reduction products of CB1954 [Boland et al, 1991; Knox et al, 1992]. The reduction of CB1954 was monitored by quantifying the increase in the area of the peak corresponding to the reduction product 5-(aziridin-1-yl)-4-hydroxylamino-2-nitrobenzamide. All the assays were initiated by addition of the enzyme and performed in duplicate. The kinetic parameters were calculated by plotting the initial rate of reduction at each concentration of CB1954 against that concentration and fitting the data to the Michaelis-Menton equation using a computer programme (Fig P). Values were confirmed by transforming the data and fitting it to various linear forms of the equation by regression analysis.

The effect of various co-substrates on CB1954 reduction was determined as above but the co-substrate was substituted for the NRH and C1954 was used at a fixed concentration of 100 μM. The enzyme concentration was 1 or 5 μg/ml. The reduction of CB1954 was monitored by measuring both the decrease in its corresponding peak area on the HPLC trace and the increase in the area of the peak corresponding to the reduction product 5-(aziridin-1-yl)-4-hydroxylamino-2-nitrobenzamide. The relative rates of reduction were determined at 10% reduction of CB1954 from a graph plotting CB1954 reduction against time. The time axis was normalised to the equivalent of 10 μg/ml of NQO2. The kinetic parameters of NQO2 for the various co-substrates was determined as for CB1954 except that the initial concentration of CB1954 was constant at 100 μm whilst that of the co-substrate was varied from 0 to 2 mM. The enzyme concentration was 0.5 μg/ml.

FIGS. 8a–c show the ability of all the compounds to act as cosubstrates.

The kinetic data determined for compounds 1 and 2 are given in Table 3.

TABLE 3

The kinetic parameters of NQO2 for various co-substrates.

| Co-substrate | $K_m$ (μM) | $k_{cat}$ (min$^{-1}$) |
|---|---|---|
| NRH | 28 ± 2 | 360 |
| 2 | 198 ± 19 | 750 |
| 1 | 1080 ± 135 | 1530 |

EXAMPLE 6

Internalisation of NQO2 Co-Substrates into Cells

Compound 1 bears a negative charge so we do not expect it to enter cells and this is what is observed. Compound 2 seems to be poorly internalised (about 10% of NRH). The poor internalisation may be due to intracellular metabolism.

The uptake of various NQO2 co-substrates into V79 cells was determined by fluorimetry. V79 cells were seeded into T25 tissue culture flasks and allowed to grow to confluence ($^-2\times10^7$ cells). The growth medium was removed and replaced with 10 mls of fresh medium containing 1 mM of co-substrate and incubated at 37° C. At various the medium was removed and the cell monolayer washed ×5 with 50 mL of ice cold PBS. The cells were removed by trypsinisation and pelleted by centrifugation. The cell pellet was resuspended in alkaline lysis buffer (KOH 0.5M; 36% W/v CsCl; in 50% aqueous ethanol) disrupted by agitation and the cell debris removed by centrifugation at 10,000 g. The concentration of co-substrate was determined by fluorimetry (excitation 360 nm, emission 450 nm, slits 5nm) by diluting 100μl of supernatant in 2.9ml of 100 mM sodium bicarbonate buffer pH 10. The fluorimeter was calibrated against the appropriate standard. All measurements were done in triplicate. The results are shown in FIG. 9.

FIG. 9 shows the uptake of various co-substrates into wild-type V79 cells. Compound 1 is charged at physiological pH and is excluded from the cells. Thus this co-substrate is suitable for MDEPT applications.

EXAMPLE 7

Cytotoxicity of CB1954 in Cells Transfected with NQO2 in the Presence of Co-Substrates We have transfected NQO2 into V79 (Chinese hamster lung embryo fibroblasts) cells and looked at the cytotoxicity of CB1954 in the presence of co-substrates.

Construction of NQO2 Vector H6

The NQO2 sequence was derived from a bacterial expression plasmid pKK-hNQO2 described in Example 1. Stages in construction were:

1) The NQO2 ORF was excised from pKK-hNQO2 as a NcoI/HindIII fragment, the NeoI site incorporating the start codon.

2) This was cloned into F58 cut NcoI/HindIII to produce the vector H1. F58 is a derivative of pBluescript II SK(+) (Stratagene) produced in house and incorporates an extra XhoI site, a Kozak sequence for good eukaryotic expression and an NcoI site (CCTCGAGTCACCATGGATATC nnn . . . ) (SEQ ID NO:1) inserted at the Bluescript EcoRV site.

Figure 10A:
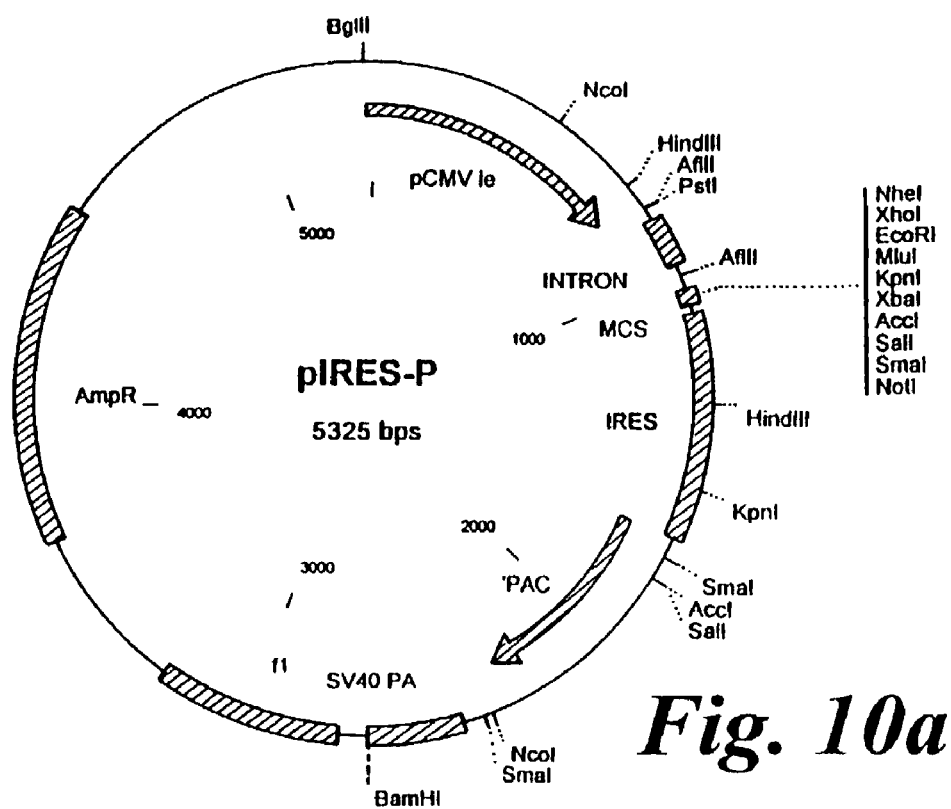
Figure 10B:
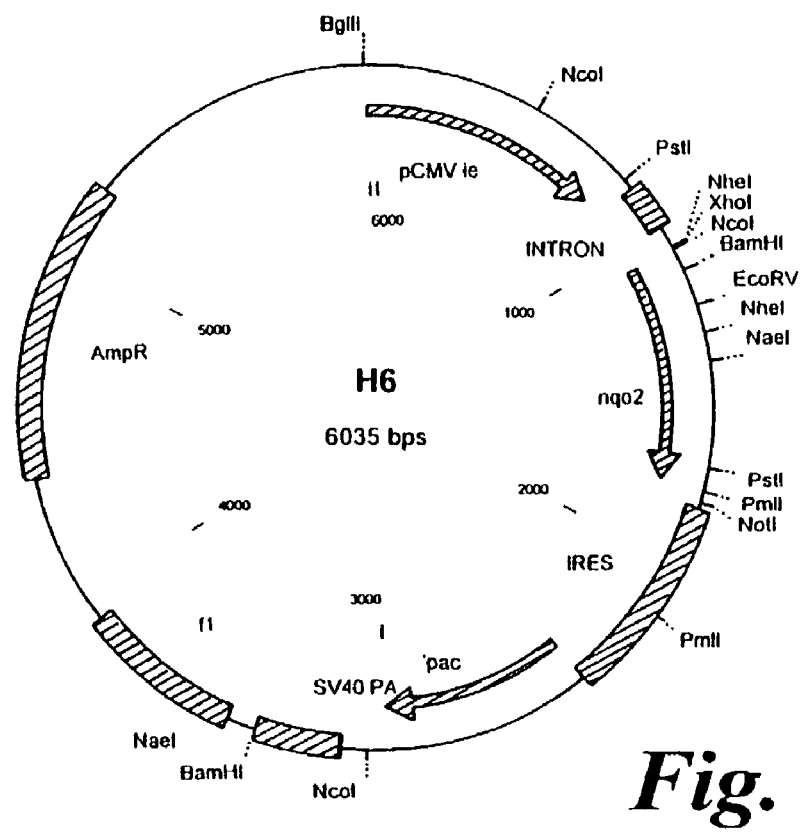

3) A partial 2 base fill was used to link the 3' HindIII site of the NQO2 ORF to the MCS XbaI site of the puromycin-resistant IRES bicistronic eukaryotic expression vector F250 (pIRES-P, EMBL:Z75185 (FIG. 10a). H1 and F250 were first cut with XhoI and the plasmid DNA purified. HI was then cut with HindIII and treated with Klenow DNA polymerase in the presence of dA+dG only, F250 was cut with XbaI and treated with Klenow and dC+dT only. The XhoI-[XbaI/CT] linearised F250 and the XhoI-[HindIII/AG] nqo2 insert were then ligated together to produce the final expression vector H6 (FIG. 10b).

Transfection of V79 Cells

Transfection quality H6 DNA was prepared using the QIAGEN endotoxin-free maxiprep kit. Chinese hamster lung embryo fibroblasts (V79) were transfected with the purified H6 using DOTAP liposomal reagent according to the manufacturer's instructions (Boehringer Mannheim). Two days after transfection puromycin-resistant clones were selected in DMEM/10% FCS containing 10 μg/ml puromycin (Sigma) and grown on to establish cell lines designated V79TM1, 5, 3, 7, 9, 11 and 13 respectively and maintained in selective medium.

Cytotoxicity Analysis in vitro

Cells in exponential phase of growth were trypsinised, seeded in 96 well plates at a density of $5 \times 10^4$ cells per well (100 μl) and permitted to recover for 24 hours. Then 50 μl of medium was removed and replaced with 50 μl of fresh medium containing 200 μM NRH to give a final concentration of 100 μM. Serial dilutions of CB 1954 (8 of 3.66×) were performed in situ giving final concentrations of 1000–0.46 μM. Cells were then incubated with drug for 72 hours at 37° C. The plates were fixed and stained with sulforhodamine-B; the absorption at 590 nm read and results were expressed as percentage of control growth. The $IC_{50}$ values were evaluated by interpolation. As a control, non-transfected V79 cells were treated as above but in this case the medium did not contain puromycin. Growth curves are shown in FIG. 11.

FIG. 11 shows the effect of NRH on the cytotoxicity of CB 1964 in NQO2 expressing V79 cells. The addition of NRH increased the cytotoxicity of CB 1954 by at least 100-fold (V79TM13) and was greater than 100-fold in the V79TM5 and 13 cell lines. This effect was not seen in non-transfected V79 cells (<3-fold) and can thus be ascribed to the expression of NQO2 in the transfected cells.

EXAMPLE 8

Cytotoxicity of CB1954 on T98G Glioblastoma Cells in the Presence of NQO2 Co-Substrate We have examined the cytotoxicity of CB1954 in the presence of either NRH, compound 1 or compound 2 on the T98G glioblastoma cell line. CB1954 alone was not toxic to these cells. CB1954 cytotoxicity was increased by at least 100-fold when cells were incubated with CB1954 and either NRH or compound 2. In the presence of compound 1, which is not able to enter the cells, no potentialtion is observed. The implication is that NQO2 is present in the cells and its activation of CB1954 is the cause of the cytotoxicity.

The results are shown in FIG. 12.

FIG. 12 shows the effect of NRH, compound 1 and compound 2 on the cytotoxicity of CB 1954 in human T98G gliobastoma cells. The cells were treated as for V79 cells but were treated for 144 hr in presence of CB 1954. The addition of NRH and compound 2 increased the cytotoxicity of CB 1954 by at least 100-fold whilst the impermeable co-substrate compound 1 did not potentiate.

EXAMPLE 9

Selectivity of NQO2 Co-Substrates and In Vivo Toxicity

Selectivity of the New Co-Substrates

FIGS. 13 and 14 show the ability of other CB1954-reducing enzymes (*E. coli* nitroreductase and rat DT diaphorase) to utilise the new co-substrates. Unlike NQO2, both of these enzymes can use NADH as a co-substrate to reduce CB1954. The data show that rat DT diaphorase is able to use both compound 1 and compound 2 as co-substrates in the reduction. However, *E. coli* nitroreductase is not able to use either. Thus the new co-substrates show a degree of selectivity and are not general electron donors.

FIGS. 15 and 16 show the effect of compound 1 on the body weight of normal mice.

FIGS. 17 and 18 show the effect of compound 2 on the body weight of normal mice. Mice (6 groups of 3) were injected intravenously (tail vein) with either compound 1 or 2 at the doses shown and the weight of the mice was monitored over an 8 day period. Control mice received vehicle (phosphate buffered saline) only.

Compounds 1 and 2 showed no evidence of intrinsic toxicity to mice as judged by body weight loss.

REFERENCES CITED

Anlezark, G. M., Melton, R. G., Sherwood, R. F., Coles, B., Friedlos, F. and Knox, R. J. (1992) "The bioactivation of 5-(aziridin-1-yl)-2,4 dinitrobenzamide (CB1954)—I. Purification and properties of a nitroreductase enzyme from *Escherichia coli*—a potential enzyme for antibody-directed enzyme prodrug therapy (ADEPT)" *Biochem Pharmacol* 44, 2289–95.

Boland, M. P., Knox, R. J. and Roberts, J. J. (1991) "The differences in kinetics of rat and human DT diaphorase result in a differential sensitivity of derived cell lines to CB 1954 (5-(aziridin-1-yl)-2,4-dinitrobenzamide)" *Biochem Pharmacol* 41, 867–75.

Chen, H. H., Ma, J. X., Forrest, G. L., Deng, P. S., Martino, P. A., Lee, T. D. and Chen, S. (1992) "Expression of rat liver NAD(P)H:quinone-acceptor oxidoreductase in *Escherichia coli* and mutagenesis in vitro at Arg-177" *Biochem J.* 284, 855–60.

Chen, S., Knox, R. J., Wu, K., Deng, P. S. K., Zhou, D., Biancher, M. A. and Amzel, L. M. (1997) "Molecular basis of the catalytic differences among DT-diaphorase of human, rat and mouse" *Journal of Biological Chemistry* 272, 1437–1439.

Connors, T. A. and Knox, R. J. (1995) "Prodrugs in medicine" *Expert Opinion on Therapeutic Patents* 5, 873–885.

Connors, T. A. and Whisson, M. E. (1966) "Cure of mice bearing advanced plasma cell tumours with aniline mustard: the relationship between glucuronidase activity and tumour sensitivity" *Nature* 210, 866–7.

Friedlos, F., Biggs, P. J., Abrahamson, J. A. and Knox, R. J. (1992a) "Potentiation of CB 1954 cytotoxicity by reduced pyridine nucleotides in human tumour cells by stimulation of DT diaphorase activity" *Biochem Pharmacol* 44, 1739–43.

Friedlos, F., Jarman, M., Davies, L. C., Boland, M. P. and Knox, R. J. (1992b) "Identification of novel reduced pyridinium derivatives as synthetic co-factors for the enzyme DT diaphorase (NAD(P)H dehydrogenase (quinone), EC 1.6.99.2)" *Biochem Pharmacol* 44, 25–31.

Friedlos, F. and Knox, R. J. (1992) "Metabolism of NAD (P)H by blood components. Relevance to bioreductively activated prodrugs in a targeted enzyme therapy system" *Biochem Pharmacol* 44, 631–5.

Jaiswal, A. K. (1994) "Human NAD(P)H:quinone oxidoreductase2. Gene structure, activity, and tissue-specific expression" *J Biol Chem* 269, 14502–8.

Jaiswal, A. K., Burnett, P., Adesnik, M. and Wesley, M. O. (1990) "Nucleotide and deduced amino acid sequence of a human cDNA (NQO-2) corresponding to a second member of the NAD(P)H: quinone oxidoreductase gene family. Extensive polymorphism at the NQO-2 gene locus on chromosome 6" *Biochemistry* 29, 1899–1906.

Knox, R. J., Friedlos, F. and Boland, M. P. (1993) "The bioactivation of CB 1954 and its use as a prodrug in antibody-directed enzyme prodrug therapy (ADEPT)" *Cancer Melastasis Rev* 12, 195–212.

Knox, R. J., Friedlos, F., Jarman, M., Davies, L. C., Goddard, P., Aniezark, G. M., Melton, R. G. and Sherwood, R. F. (1995) "Virtual cofactors for an *Escherichia-coli* nitroreductase enzyme—relevance to reductively activated prodrugs in antibody-directed enzyme prodrug therapy (adept)" *Biochemical Pliarmacology* 49, 1641–1647.

Knox, R. J., Friedlos, F., Sherwood, R. F., Melton, R. G. and Anlezark, G. M. (1992) "The bioactivation of 5-(aziridin-1-yl)-2,4-dinitrobenzamide (CB1954)—II. A comparison of an *Escherichia coli* nitroreductase and Walker DT diaphorase" *Biochem Pharmacol* 44, 2297–301.

Mauger, A. B., Burke, P. J., Somani, H. H., Friedlos, F. and Knox, R. J. (1994) "Self-immolative prodrugs: candidates for antibody-directed enzyme prodrug therapy in conjunction with a nitroreductase enzyme" *J Med Chem* 37, 3452–8.

Quinn, J. (1996) "Studies on CB1954 and its analogues" *PhD Thesis*: University of London.

Sharma, S. K., Bagshawe, K. D., Burke, P. J., Boden, R. W and Rogers, G. T. (1990) "Inactivation and clearance of an anti-CEA carboxypeptidase G2 conjugate in blood after localisation in a xenograft model" *Br. J. Cancer* 61, 659–662.

Whisson, M. E. and Connors, T. A. (1965) "Cure of mice bearing advanced plasma cell tumours with aniline mustard" *Nature* 206, 689–91.

The invention claimed is:

1. A therapeutic system comprising a prodrug which is converted to a substantially cytotoxic drug by the action of NQO2, at intracellular sites where NQO2 is expressed, and a compound of formula I

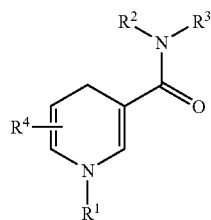

wherein R1 is selected from the group consisting of substituted alkyl, including substitution by $CONH_2$, OH, halogen, CN, and COOH; aryl; substituted aryl; $CONR_aR_b$, where $R_a$ and $R_b$ are independently H, alkyl, or substituted alkyl, and $R^2$ and $R^3$ are independently H, alkyl, or substituted alkyl and $R^4$ is any of H, alkyl, substituted alkyl, halogen, CN, COOH, $CONH_2$, or OH, wherein the compound can pass reducing equivalents to NQO2, in a form for administration to a patient in need thereof, wherein the prodrug is CB 1954.

2. The system of claim 1, wherein the compound is 1-(carboxamidomethyl)-dihydronicotinamide.

3. The system of claim 1, wherein the compound has formula II

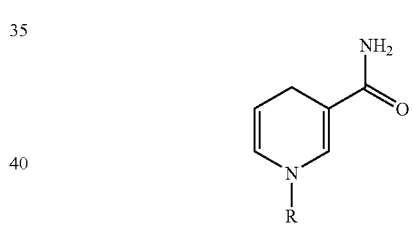

wherein R is a substituted alkyl, comprising one or more groups selected from the group consisting of $CONH_2$, OH, halogen, CN, and COGH.

4. The system of claim 1, wherein the alkyl group is a C1 to C6 alkyl.

5. The system of claim 3, wherein R is selected from the group consisting of —$CH_2CONH_2$, —$CH_2CH_2CH_2SO_3^-$, —$CH_2CH_2OH$, —$CH_2CH_2CH_2OH$, and —$CH_2CH_2COOH$.

6. The therapeutic system of claim 1 wherein the system is effective at killing tumor cells in the treatment of cancer.

* * * * *

UNITED STATES PATENT AND TRADEMARK OFFICE
CERTIFICATE OF CORRECTION

| | | |
|---|---|---|
| PATENT NO. | : 7,138,122 B2 | Page 1 of 1 |
| APPLICATION NO. | : 10/099830 | |
| DATED | : November 21, 2006 | |
| INVENTOR(S) | : Philip John Burke and Richard John Knox | |

It is certified that error appears in the above-identified patent and that said Letters Patent is hereby corrected as shown below:

Claim 3, column 38, line 47, replace "COGH" with --COOH--.

Signed and Sealed this

Fourth Day of December, 2007

JON W. DUDAS
*Director of the United States Patent and Trademark Office*

SEQUENCE LISTING

```
<160> NUMBER OF SEQ ID NOS: 2

<210> SEQ ID NO 1
<211> LENGTH: 24
<212> TYPE: DNA
<213> ORGANISM: Artificial Sequence
<220> FEATURE:
<223> OTHER INFORMATION: nucleotide incorporating XhoI, Kozak sequence,
      and NcoI site
<220> FEATURE:
<221> NAME/KEY: misc_feature
<222> LOCATION: (22)..(24)
<223> OTHER INFORMATION: n at positions 22, 23 and 24 can be any
      nucleotide

<400> SEQUENCE: 1
cctcgagtca ccatggatat cnnn                                          24

<210> SEQ ID NO 2
<211> LENGTH: 697
<212> TYPE: DNA
<213> ORGANISM: Homo sapiens
<220> FEATURE:
```

<221> NAME/KEY: misc_feature
<223> OTHER INFORMATION: cDNA encoding human NAD(P)H:quinone reductase
      2 (NQO2)

<400> SEQUENCE: 2

```
atggcaggta agaaagtact cattgtctat gcacaccagg aacccaagtc tttcaacgga    60
tccttgaaga atgtggctgt agatgaactg agcaggcagg gctgcaccgt cacagtgtct   120
gatttgtatg ccatgaactt tgagccgagg gccacagaca aagatatcac tggtactctt   180
tctaatcctg aggttttcaa ttatggagtg gaaacccacg aagcctacaa gcaaaggtct   240
ctggctagcg acatcactga tgagcagaaa aaggttcgga ggctgaccta gtgatatttc   300
agttcccgct gtactggttc agcgtgccgg ccatcctgaa gggctggatg gatagggtgc   360
tgtgccaggg ctttgccttt gacatcccag gattctacga ttccggtttg ctccagggta   420
aactagcgct cctttccgta accacgggag gcacggccga gatgtacacg aagacaggag   480
tcaatggaga ttctcgatac ttcctgtggc cactccagca tggcacatta cacttctgtg   540
gatttaaagt ccttgcccct cagatcagct ttgctcctga aattgcatcc gaagaagaaa   600 gaaggggat ggtggctgcg tggtcccaga ggctgcagac catctggaag gaagagccca   660
tcccctgcac agcccactgg cacttcgggc aataact                             697
```